(12) United States Patent
Muller et al.

(10) Patent No.: US 7,223,395 B2
(45) Date of Patent: May 29, 2007

(54) BLOCKING LEUKOCYTE EMIGRATION AND INFLAMMATION BY INTERFERING WITH CD99/HEC2

(75) Inventors: William A. Muller, Port Washington, NY (US); Alan R. Schenkel, Ft. Collins, CO (US)

(73) Assignee: Cornell Research Foundation, Inc., Ithaca, NY (US)

( * ) Notice: Subject to any disclaimer, the term of this patent is extended or adjusted under 35 U.S.C. 154(b) by 274 days.

(21) Appl. No.: 10/221,758

(22) PCT Filed: Mar. 13, 2001

(86) PCT No.: PCT/US01/07963

§ 371 (c)(1),
(2), (4) Date: Mar. 27, 2003

(87) PCT Pub. No.: WO01/68131

PCT Pub. Date: Sep. 20, 2001

(65) Prior Publication Data

US 2003/0211099 A1    Nov. 13, 2003

Related U.S. Application Data

(60) Provisional application No. 60/188,804, filed on Mar. 13, 2000.

(51) Int. Cl.
*A61K 39/395*    (2006.01)
(52) U.S. Cl. .................................. 424/144.1; 424/154.1
(58) Field of Classification Search .................. 435/7.1; 424/144.1, 154.1
See application file for complete search history.

(56) References Cited

FOREIGN PATENT DOCUMENTS

WO    WO89/12690    12/1989
WO    WO 96/27613 A    9/1996

OTHER PUBLICATIONS

Bixel et al. Mouse CD99 participates in T-cell recruitment into inflamed skin. Blood. Nov. 15, 2004;104(10):3205-13.*
Sherman-Gold, Gen. Eng. News 1993.*
http://www-users.med.cornell.edu/~jawagne/Antibody_Approaches.html, Making and using antibodies, May 31, 2005, pp. 1-7.*
Norman and Kubes. Therapeutic intervention in inflammatory diseases: a time and place for anti-adhesion therapy. Microcirculation. Jan.-Feb. 2005;12(1):91-8.*
Smith et al. "The Genomic Organisation of the Human Pseudoautosomal Gene *MIC2* and the Detection of a Related Locus", *Human Molecular Genetics* (1993), vol. 2, No. 4, 417-422.
Bernard et al., "Apoptosis of Immature Thymocytes Mediated by E2/CD99[1]", *The Journal of Immunology* (1997), 158: 2543-2550.
Bernard et al., "The E2 Molecule (CD99) Specifically Triggers Homotypic Aggregation of $CD4^+CD8^+$Thymocytes", *The Journal of mmunology* (1995), 154: 26-32.
Banting et a ., "The *MIC2* Gene Product: Epitope Mapping and Structural Prediction Analysis Define An Integral Membrane Protein", *Molecular Immunology* (1989), 26:(2) 181-188.
Hahn et al., "CD99 (*MIC2*) Regulates the LFA-1/ICAM-1-Mediated Adhesion of Lymphocytes, and Its Gene Encodes Both Positive and Negative Regulators of Cellular Adhesion[1]" *The Journal of Immunology* (1997), 159 (5) 2250-2258.
Petit et al., "Physical Mapping of the Human Pseudo-Autosomal Region; Comparison with Genetic Linkage Map" *The EMBO Journal* (1998) vol. 7, No. 8 2369-2376.
Dworzak et al., "Flow Cytometric Assessment of Human-MIC2 Expression In Bone Marrow, Thymus, and Peripheral Blood" *Blood*, (1994) vol. 83, No. 2 415-425.
Aubrit et al., "The Biochemical Characterization of E2, a T Cell Surface Molecule Involved in Rosettes" *Eur. J. Immunol.* (1989), 19:1431-1436.
Waclavicek et al., "CD99 Engagement on Human Peripheral Blood T Cells Results in TCR/CD3-Dependent Cellular Activation and Allows for Th1-Restricted Cytokine Production[1]", *The Journal of Immunology* (1988), 161: 4871-4878.
Ellis et al., "*PBDX* is the XG Blood Group Gene", *Nature Genetics* (1994), vol. 8, 285-290.
Muller et al , "Monocyte-Selective Transendothelial Migration: Dissection of the Binding and Transmigration Phases by an In Vitro Assay", *J. Exp. Med.* (1992), vol. 176, 819-828.
Muller et a ., "A Human Endothelial Cell-Restricted, Externally Disposed Plasmalemmal Protein Enriched in Intercellular Junctions", *J. Exp. Med.* (1989), vol. 170, 399-414.
Muller et al . "The Membrane Proteins of the Vacuolar System I. Analysis by a Novel Method fo Intralysosomal Iodination", *The Journal of Cel. Biology* (1980), vol. 86, 292-303.
Muller et a ., "Plasmalemmal Proteins of Cultured Vascular Endothelial Cells Exhibit Apical-Basal Polarity: Analysis by Surface-Selective Indination", *The Journal of Cell Biology* (1986), vol. 103, No. 6., 2389-2402.
Muller et al., "The Membrane Proteins of the Vascuolar System II. Bidirectional Flow between Secondary Lysosomes and Plasme Membrane", *The Journal of Cell Biology* (1980), vol. 86, 304-314.

(Continued)

*Primary Examiner*—Maher M. Haddad
(74) *Attorney, Agent, or Firm*—Darby & Darby

(57) ABSTRACT

The present invention provides methods and compositions for modulating transendothelial migration (TEM) of leukocytes. In particular, inhibition of TEM can provide a potent therapeutic approach to treating inflammatory conditions. The invention specifically relates to the discovery that CD99 mediates TEM, because blocking CD99 on either endothelial cells or monocytes bloks migration 80-90%. In conjunction with PECAM inhibitors, TEM blockade approaches 100%. CD99 is involved in a step in TEM that is distal to the step controlled by PECAM.

13 Claims, 5 Drawing Sheets

OTHER PUBLICATIONS

C. Gelin et al., "The E2 antigen, a 32 kd glycoprotein involved in T-cell adhesion processes, is the MIC2 gene product," EMBO Journal 11:3253-3259 (1989).

E. Y. Choi et al., "Engagement of CD99 Induces Up-Regulation of TCR and MHC Class I and II Molecules on the Surface of Human Thymocytes" Journal of Immunology, vol. 161, No. 2, pp. 749-754, Jul. 15, 1998.

G. S. Duncan et al., "Genetic Evidence for Functional Redundancy of Platelet/Endothelial Cell Adhesion Molecule-1 (FECAM-1): CD31-Deficient Mice Reveal PECAM-1-Dependent and PECAM-1-Independent Functions" Journal of Immunology, vol. 162, No. 5, pp. 3022-3030, Mar. 1, 1999.

D. Wingett et al., "A Role for CD99 in T Cell Activation" Cellular Immunology, vol. 193, No. 1, pp. 17-23, Apr. 10, 1999.

C. K. Park et al., "High CD99 Expression in Memory T and B Cells in Reactive Lymph Nodes" Journal of Korean Medical Science, vol. 14, No. 6, pp. 600-606, Dec. 1999.

Gabriele Bixel et al.; Mouse CD99 participates in T-cell recruitment into inflamed skin; *Blood*, Nov. 15, 2004;104(10): 3205-3213.

Christopher V. Carman, and Timothy A. Springer.; A transmigratory cup in leukocyte diapedesis both through individual vascular endothelial cells and between them; *JCB*; 2004;167(2): 378-388.

\* cited by examiner

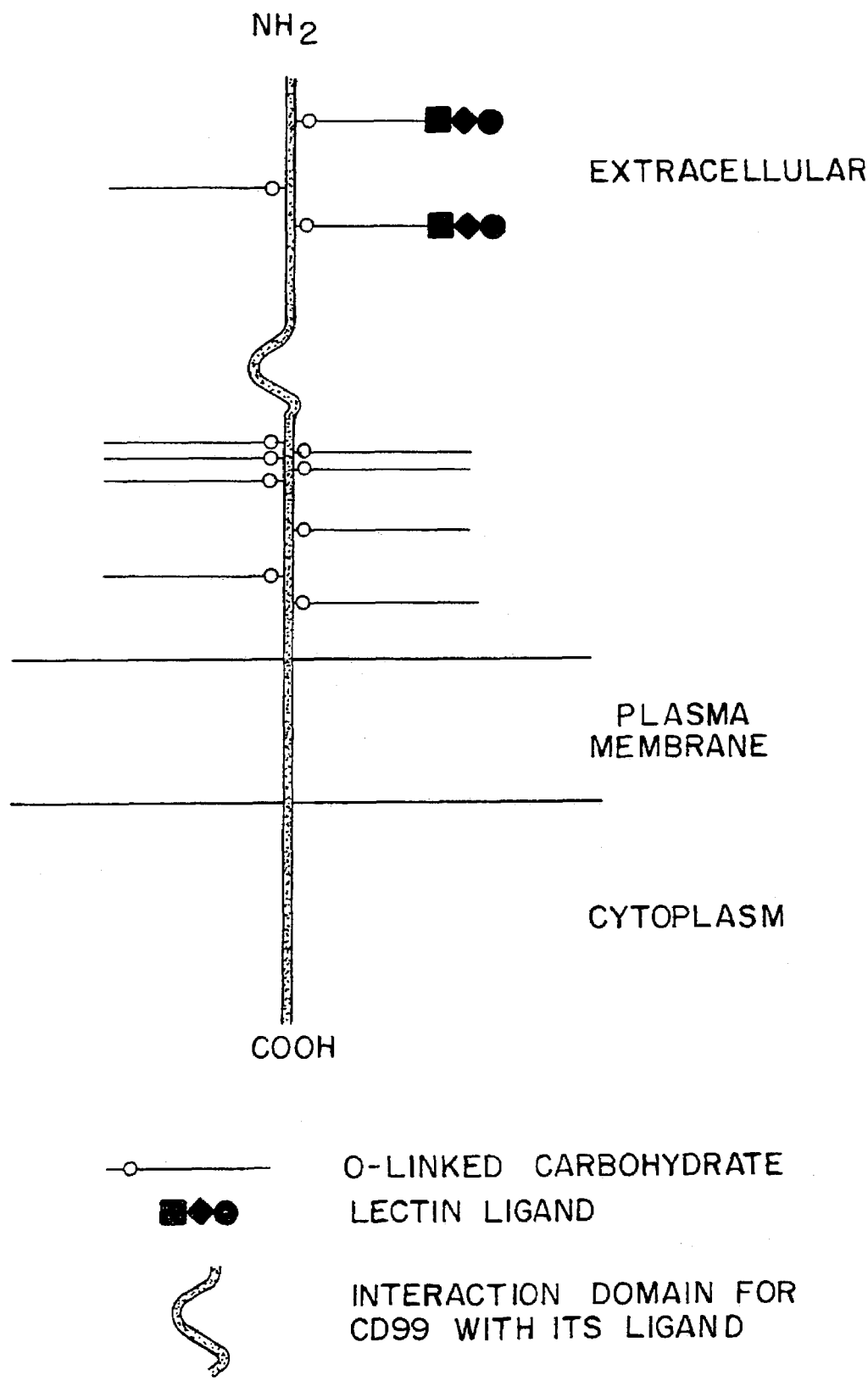

BLOCKING LEUKOCYTE EMIGRATION AND INFLAMMATION BY INTERFERING WITH CD99/HEC2

This application claims priority under 35 U.S.C. § 119(e) to provisional application Ser. No. 60/188,804, filed Mar. 13, 2000, which is incorporated herein by reference in its entirety.

The research leading to the present invention was supported, in part, by Grant No. HL64774 from the National Institutes of Health. Accordingly, the United States Government may have certain rights in the invention.

FIELD OF THE INVENTION

This invention concerns anti-inflammatory processes, in particular modulating transendothelial migration of leukocytes, and compositions for blocking transendothelial migration of leukocytes.

BACKGROUND OF THE INVENTION

References cited throughout this specification by number are listed at the end of the Examples in the section "REFERENCES".

Previous studies (1-12) have demonstrated a crucial role for platelet/endothelial cell adhesion molecule-1 [PECAM] in transendothelial migration [TEM] of neutrophils [PMN], monocytes [Mo], and natural killer [NK] cells. However, even under the most favorable circumstances, anti-PECAM reagents block only 80-90% of leukocyte influx. While this is as good or better a block of inflammation as has been achieved by targeting a single molecule, the residual 10-20% of leukocytes that are not blocked may represent a clinically significant population under chronic conditions. Furthermore, there are at least some inflammatory models in which PECAM does not appear to play a role. Most important for the present invention, there may be stages in TEM that are mediated by molecules other than PECAM, which await discovery.

Leukocyte Migration in Inflammation

Migration of leukocytes into a site of inflammation involves several steps mediated by several families of adhesion molecules. We have focused on the step of transendothelial migration [TEM] because it is the step at which leukocytes become irreversibly committed to entering the inflamed tissues. We have previously described the critical role of PECAM, expressed on the surfaces of all Mo and PMN and concentrated at the borders of endothelial cells, in TEM. Under the best-controlled conditions, anti-PECAM reagents block 80-90% of TEM in in vitro and in many in vivo models. However, there are consistently at least 10-20% of leukocytes that escape this blockade (1,2,4,6,8). Furthermore, at least one in vivo model has been described in which antibody against PECAM has no effect (9). Targeted deletion of PECAM results in mice with no significant defects in their acute inflammatory response (26). Therefore, mechanisms of TEM independent of PECAM exist. Knowing these mechanisms will lead to a better understanding of inflammation. Targeting these pathways may be a useful adjunct to anti-inflammatory therapies aimed at PECAM.

Molecularly Dissectable Steps in Leukocyte Emigration

The inflammatory response is a double-edged sword. Mobilization of leukocytes to a focus of inflammation is critical for the rapid resolution of infections and restoration of tissue damage resulting from a variety of injuries. On the other hand, most human pathology results from inflammation that is misdirected or prolonged with the result that host tissues are damaged. Common examples include the inflammatory arthropathies, pulmonary fibrosis, and atherosclerosis, which is currently viewed as a chronic inflammatory disease of the arterial wall (13). Therefore, much attention has been directed toward understanding inflammation at the molecular level in the hopes of being able to better regulate it.

The process of leukocyte emigration has been dissected into a series of sequential adhesion events in the following working model [See FIG. 1]. We can divide leukocyte emigration into these steps because we have reagents that can block each one of these steps. There may be additional adhesion molecules awaiting discovery that interact at steps intermediate to or distal to these. Indeed, CD99 may be just such a molecule.

Rolling. In the first step, some of the leukocytes entering a postcapillary venule in an area of inflammation leave the circulatory stream and adhere loosely, tentatively, and reversibly to the endothelial cell surfaces in a process aptly named "rolling." The selection family of adhesion molecules and their sialylated-Lewis$^x$-decorated ligands appear to be primarily responsible for this initial interaction [reviewed in (14,15)]. Rolling leukocytes come into direct contact with the endothelium, exposing them to a variety of signals capable of promoting the next step—activating the leukocyte-specific integrins. The binding of leukocytes to E-selectin itself may be a sufficient signal (16). Alternatively or additionally, the leukocytes tethered by selectins are now in a position to be activated by platelet activating factor (17) or other lipid modulators (18), chemokines bound to endothelial surface glycosaminoglycans (19), soluble chemoattractants (20), or ligands that cross-link leukocyte CD31 (3,21,22).

Adhesion. Upon activation of their integrins to the high affinity binding state, leukocytes cease rolling and adhere tightly to the endothelial surface. For monocytes and lymphocytes, which express integrins of the both β1 and β2 families, engagement by either integrin may suffice to promote attachment for subsequent transmigration (23). The identified counter-receptors for β1 and β2 integrin-mediated adhesion include ICAM-1, ICAM-2, and VCAM-1, members of the immunoglobulin gene superfamily. Leukocytes bound tightly to the luminal surface of the endothelial cell crawl rapidly to an intercellular junction, a process that requires successive cycles of adhesion and dis-adhesion, as the leukocytes attach at their forward ends and release at their rear.

Transmigration. Upon reaching the junction, they insert pseudopods between tightly apposed endothelial cells and crawl through, in ameboid fashion, while retaining tight contacts with the endothelial cell. This step is referred to as diapedesis, transendothelial migration [TEM], or transmigration. Platelet/endothelial cell adhesion molecule-1 [PECAM, also known as CD31], a CAM of the immunoglobulin superfamily (24), expressed on the surfaces of leukocytes and platelets and concentrated in the borders between endothelial cells, is involved in this step. Contact between leukocyte PECAM and endothelial PECAM is crucial for the transmigration of the vast majority of neutrophils and monocytes in vitro (1) and in vivo (2,8). We can inhibit TEM in vitro and in vivo by administering agents that interfere with the homophilic interaction of leukocyte PECAM with endothelial PECAM. These include mAb that bind to PECAM domain 1 and/or 2 and block this critical site, or soluble recombinant PECAM-IgG chimeras containing at least domain 1, which competitively inhibit this interaction (4,6, 25). Therefore, PECAM-dependent transmigration is a promising target for anti-inflammatory therapy.

In summary, while we have learned a great deal about the molecules and mechanisms of leukocyte rolling and adhesion to the apical surface of endothelium (15,46,47), there is a big gap in our present knowledge of transendothelial migration. PECAM clearly plays an important role in TEM for most PMN and monocytes under most inflammatory conditions studied to date. The function of PECAM in mediating transmigration without affecting apical adhesion defines TEM as a separate step in leukocyte emigration. However, while PECAM is the only molecule that has been identified to play a unique role in TEM, it is clearly not the only molecule involved in TEM.

CD99

CD99 was discovered and pursued independently by four separate sets of investigators. It was identified by geneticists as the only known human pseudoautosomal gene; its gene product defines the Xg(a+) blood type. Similar to the case with the Duffy blood group, Xg(a−) individuals lack CD99 on their RBC, but express it appropriately on other cell types. The gene is located on the distal end of the short arm of the X chromosome, a region involved in pairing with a short homologous region of the Y chromosome during meiosis. Due to this phenomenon, cross-over of these regions of the X and Y chromosome led to duplication of this gene on the Y chromosome and inheritance of this gene similar to an autosomal trait, hence the name "pseudoautosomal." In mice several genes have been identified to be inherited this way. CD99 is the only example in humans thus far.

The surgical pathology literature is replete with references to CD99, since it was found to be a reliable marker to distinguish Ewing's sarcoma from other "small round blue cell" tumors. However, the function of the molecule on the surfaces of these tumors is completely unknown. Its function is best characterized on T cells, where it was found to be an alternative ligand to CD2 for the phenomenon of sheep red blood cell rosetting. In addition, ligation of CD99 on thymocytes and T cells has been shown to play a costimulatory function in certain in vitro models. These latter two functions will be discussed in more detail below, since they are the most relevant to a role for CD99 in leukocyte transmigration.

One of the problems confronting CD99 research is that several of the existing CD99 mAb only react with epitopes expressed by immature thymocytes; other mAbs react with only certain peripheral blood leukocyte types due to post-translational modifications of the molecule. Of the few published reports about CD99 on leukocytes, none use the same cell type or the same antibody, making comparisons difficult. For example, the VIth International Leukocyte Typing Workshop chapter on CD99 states that CD99 is not expressed on monocytes or platelets. Furthermore, one of the major publications on CD99 states that the molecule is not expressed by granulocytes.

The cDNA encoding CD99 predicts a type I transmembrane protein of 16.7 kd that spans the membrane once. There are no consensus N-linked glycosylation sites, but several sites for O-linked glycosylation, which accounts for 14 kd of its apparent molecular weight of 32 kd. Indeed, treatment with O-glycanase reduces its Mr to 18 kd (Aubrit et al., Eur. J. Immunol. 1989, 19:1431). There is a proline-rich region near the mature amino terminus and a stretch of five Gly-X-Y repeats following that. However, there are no proline residues in these repeats, making it extremely unlikely that it functions as a "collagen-like" protein. CD99 is not a member of any known protein family, nor is it remotely homologous to any known protein except for 48% homology to PBDX, the product of a gene located adjacent to CD99 on the X chromosome and involved in the expression of CD99 on erythrocytes (Ellis et al., Nature Genetic, 1994, 8:285). There are only two methionine residues and one cysteine residue (on the cytoplasmic side) in the molecule, consistent with difficulty with metabolic labeling using these amino acids (see, page 37). The single cytoplasmic tyrosine residue is predicted to be the first amino acid on the cytoplasmic surface of the membrane, making it unlikely that it will play a role in known phosphotyrosine signaling cascades.

Gelin, et al. (EMBO J, 1989, 8:3252) found that while the majority of spontaneous sheep (and human) RBC adhesion to human T cells was mediated by CD2/LFA-3 interactions, significant residual adhesion took place in the presence of optimal CD2 blockade. This was due to interactions between CD99 on the T cell and some other molecules(s) on the RBC. Since RBC normally express CD99, the way this was demonstrated was to show that a) anti-CD99 mAb absorbed to the RBC did not block binding, while the same mAb bound to the T cells did, and b) normal T cells rosetted with Xg(a−) RBC that do not express CD99, as well as they did with Xg(a+) RBC, which express it. While the rosetting effect was small compared to the extent of rosetting by CD2, this demonstrates that CD99 is capable of adhesive interactions in a heterophilic manner.

The other reports on CD99 that are potentially relevant to this project involve cross-linking CD99 on the surfaces of thymocytes or T cells. In the Jurkat T cell line, cross-linking surface-bound CD99 mAb with a polyclonal anti-mouse antibody led to a rapid (<30 min.) increase in the surface expression of LFA-1 (CD11a/CD18) and stimulation of LFA-1/ICAM-1-dependent homotypic aggregation (Hahn et al., J. Immunol. 1997; 159:2550). The same treatment of immature (CD4$^+$CD8$^+$) thymocytes led to a similar rapid increase in surface T cell receptor and MHC Class I expression, which was believed to come from intracellular pools (Choi et al., J. Immunol. 1998; 161:745). Experiments using peripheral blood T cells showed that extensive cross-linking of CD99 (by plate-bound mAb) provided a costimulatory signal for intracellular Ca$^{++}$ flux, CD25 expression, and proliferation under conditions of suboptimal cross-linking by anti-CD3 (Waclavicek et al., J. Immunol. 1998; 161: 4671; Wingett et al., Cell. Immunol. 1999; 193:17). In all of these instances, the effects of the anti-CD99 mAb were small compared to those achieved by activating classical costimulatory molecules such as CD28. However, they demonstrate that CD99 is capable of functioning as a signaling molecule, either directly or indirectly, upon engagement.

The ligand(s) for CD99 are not known. Since it is not a member of any known molecular family, it is impossible to make first guesses about its ligands and mechanisms of action based on experience with related family members.

The present invention sheds more light on the process of transmigration, and on the function of CD99. In so doing, it elucidates an important inflammatory mechanism, and thus a strategy for modulating inflammation.

BRIEF DESCRIPTION OF THE DRAWINGS

FIG. 4 is a schematic drawing depicting the CD99 protein in the plasma membrane; its carbohydrate modifications and its ligand interaction domains are indicated.

DETAILED DESCRIPTION

The present invention is based, in part, on identification of a 30 kD membrane protein expressed at the borders between confluent endothelial cells as well as on the surfaces of leukocytes. This protein has been identified as CD99. In our in vitro assay, a monoclonal antibody [mAb] against this molecule selectively blocks TEM of monocytes and, to a lesser extent, PMN, independent of their ability to adhere to the apical surface of endothelium. Considering that the published effects of anti-CD99 mAb are quantitatively small, it is quite possible that the most important physiologic function(s) of CD99 may be related to leukocyte transmigration, where mAb hec2 blocks transmigration by greater than about 90%.

Two murine models of acute inflammation in which the effect of blocking mAb can be assessed both quantitatively and qualitatively, can show that the block produced by interfering with these molecules is at the level of TEM or adhesion. The role of CD99/HEC2 is evaluated in wild-type mice as well as in mice in which PECAM is maximally blocked. CD99 activity can also be tested in any of three lines of mice in which PECAM is either absent or nonfunctional, and therefore TEM occurs independently of PECAM. PECAM-independent or alternative pathways will be easier to identify in such mice. The effects of blocking mAb to these new molecules are tested in wild-type mice to determine the effect of blocking these molecules by themselves; Tg8 mice that constitutively express circulating PECAM-IgG and have a maximal block of PECAM function; PECAM deficient [knockout] mice, which have no PECAM; and Tg5 and Tg11 mice that constitutively express supratherapeutic levels of soluble PECAM-1 and are refractory to its effects, despite having normal levels of PECAM on their endothelial cells and leukocytes. These studies provide a better understanding of the molecules and mechanisms involved in transendothelial migration of leukocytes and identify additional therapeutic compounds for anti-inflammatory therapy.

Thus, this invention advantageously addresses PECAM-independent TEM. More specifically, it considers molecules that function at a different stage or step in TEM that are totally independent of PECAM, such as CD99/HEC2. It also considers molecules that mediate residual TEM that occurs when PECAM is blocked, which may act at the same stage or step as PECAM. CD99/HEC2 likely plays a role here as well; this molecule is well known, as described in the BACKGROUND supra.

Figure 1:
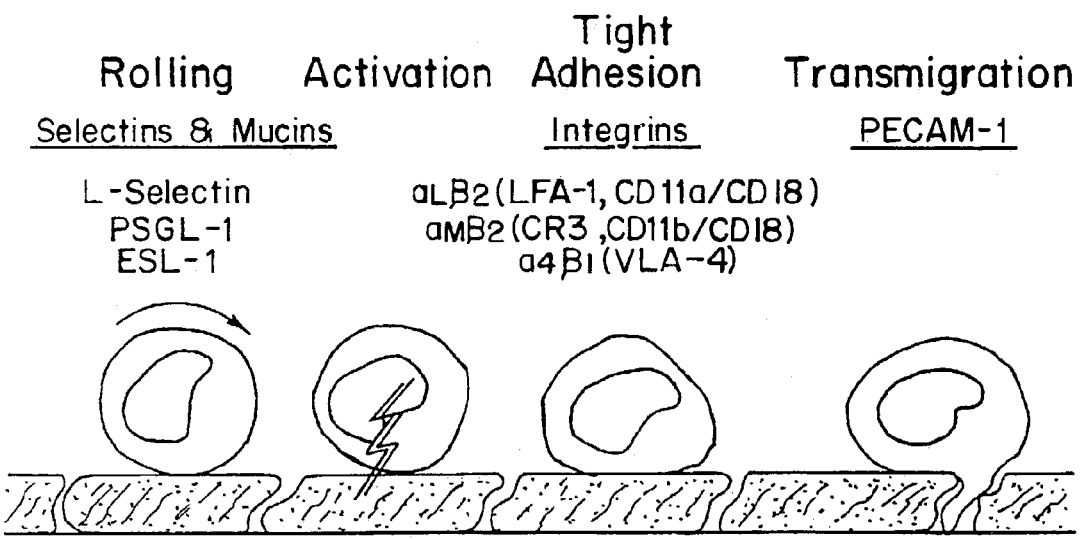
FIG. 1 shows the adhesion steps in leukocyte emigration.

As used herein, the term "transendothelial migration" (TEM) refers to the movement of leukocytes from the apical surface to the basal lamina of endothelial cells and beyond in response to chemotactic factors (when such factors are present at a higher concentration at the basal lamina than at the apical surface of the endothelial cells). Leukocytes migrate between junctions formed in the endothelium between individual endothelial cells. FIG. 1 schematically illustrates this process. Generally, TEM occurs when the endothelial cells are activated, e.g., with TNF, IL-1, or other pro-inflammatory mediators. TEM can also occur endogenously, and will occur at a lower, less robust level across endothelial cells as a consequence of leukocyte adhesion even in the absence of direct activation of the endothelial cells. Thus, TEM occurs in vivo at inflammatory foci; and in vitro, across cultured endothelial cells preferably after activation of the endothelial cells and/or creating a chemotactic gradient. The inventors have found that the in vitro system replicates inflammatory conditions in vivo for studying TEM with a high degree of predictability.

The term "leukocytes" includes, but is not limited to, polymorphonuclear leukocytes (i.e., neutrophils), monocytes (which differentiate into dendritic cells or macrophages after transmigration into a site to which they are attracted), granulocytes (including eosinophils and basophils), natural killer cells and lymphocytes, e.g., T lymphocytes, as well as circulating dendritic cell precursors.

The term "endothelial cell" (or EC) has ordinary meaning in the art. Endothelial cells make up endothelium, which is found inter alia in the lumen of vascular tissue (veins, arteries, and capillaries) throughout the body. The "apical surface" of endothelium is the lumenal surface, i.e., in contact with blood. The basal lamina or basement membrane is the layer of extracellular matrix that separates the endothelium from the wall of the vessel. In most cases of inflammation, leukocytes emigrate across post-capillary venules whose wall consists of a discontinuous layer of vascular smooth muscle cells that separate the vessel from the tissue it is supplying.

Activation of endothelial cells can result from contact with stimulatory mediators. For purposes of the present invention, activation of endothelial cells results from contact with pro-inflammatory cytokines such as, but not limited to, tumor necrosis factor (TNF) and interleukin-1 (IL-1), particularly IL-1β.

The present invention encompasses assessing CD99-mediated TEM and compounds that are candidate inhibitors of this process in assays in vitro and in vivo. For the in vitro assays, the endothelial cells are preferably cultured on a permeable membrane or collagen gel. In vivo, TEM occurs at a site of inflammation, which can be induced (e.g., with thioglycollate or croton oil treatment) or result from a natural inflammatory condition (infection, wound, autoimmunity).

An "inhibitor of CD99" is a molecule that blocks or reduces binding of CD99 to itself or its heterophilic binding partner (i.e., CD99 ligand or CD99 receptor), i.e., prevents CD99 from interacting with (e.g., binding to) the heterophilic or homophilic binding partner and mediating TEM. In a specific embodiment, an anti-CD99 monoclonal antibody molecule is such an inhibitor. Alternatively, an extracelluar fragment of CD99 (see FIG. 4) is an inhibitor, and more particularly, a competitive inhibitor. An "extracellular fragment of CD99" can be the entire extracellular domain, i.e., from the N-terminus to about the start of the transmembrane domain, or a smaller portion thereof comprising an interaction domain of CD99 with its binding partner (including chimeric constricts of the CD99 extracellular domain, e.g., with an immunoglobulin molecule); a carbohydrate, particularly an O-linked carbohydrate; or a lectin ligand. Thus, suitable inhibitors can interact with CD99 carbohydrates; such inhibitors can be various lectins. Alternatively, soluble carbohydrates or carbohydrate mimetics can be used to block the lectin that interacts with critical carbohydrates on CD99. Similarly, peptides or peptidomimetics can block interaction with a polypeptide interaction domain of CD99. Furthermore, combinations of the foregoing can, under certain circumstances, prove most effective at inhibiting CD99. In a specific embodiment, such an inhibitor is an anti-CD99 antibody molecule, more specifically, an anti-CD99 monoclonal antibody molecule.

The term anti-CD99 antibody molecule includes immunoglobins that recognize CD99/HEC2 homologues of mice, human beings or other species, derivatives of such antibodies with at least the ligand binding portion of the CD99/HEC2 homologues mentioned, may be used as well, including, but not limited to, single chain, Fv, Fab, Fab', F[ab']$_2$, chimeric antibodies, humanized antibodies and the like.

The term "inflammatory condition" refers to either an acute or chronic inflammatory condition, which can result from infections or non-infectious causes. Various infectious conditions include meningitis, encephalitis, uveitis, colitis, dermatitis, and adult respiratory distress syndrome. Non-infectious causes include trauma (burns, cuts, contusions, crush injuries), autoimmune diseases, and organ rejection episodes. Thus, in specific embodiments, an inflammatory condition results from a condition selected from the group that includes: atherosclerosis (arteriosclerosis); autoimmune conditions, such as multiple sclerosis, systemic lupus erythematosus, polymyalgia rheumatica (PMR), rheumatoid arthritis and other forms of inflammatory arthritis, Sjogren's Syndrome, progressive systemic sclerosis (scleroderma), ankylosing spondylitis, polymyositis, dermatomyositis, pemphigus, pemphigoid, Type I diabetes mellitus, myasthenia gravis, Hashimoto's thyroditis, Graves' disease, Goodpasture's disease, mixed connective tissue disease, sclerosing cholangitis, inflammatory bowel disease including Crohn's Disease (regional enteritis) and ulcerative colitis, pernicious anemia, inflammatory dermatoses; usual interstitial pneumonitis (UIP), asbestosis, silicosis, berylliosis, talcosis, the various forms all forms of pneumoconiosis, sarcoidosis (in the lung and in any other organ), desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa); inflammatory dermatoses not presumed to be autoimmune; chronic active hepatitis: delayed-type hypersensitivity reactions (e.g., poison ivy dermatitis); pneumonia or other respiratory tract inflammation due to any cause; Adult Respiratory Distress Syndrome (ARDS) from any etiology; encephalitis, with inflammatory edema; immediate hypersensitivity reactions including, but not limited to, asthma, hayfever, cutaneous allergies, acute anaphylaxis; diseases involving acute deposition of immune complexes, including, but not limited to, rheumatic fever, acute and/or chronic glomerulonephritis due to any etiology, including specifically post-infectious (e.g., post-Streptococcal) glomerulonephritis, acute exacerbations of Systemic Lupus Erythematosus; pyelonephritis; cellulitis; cystitis; acute cholecystitis; and conditions producing transient ischemia anywhere along the gastrointestinal tract, bladder, heart, or other organ especially those prone to rupture; sequelae of organ transplantation or tissue allograft, including allograft rejection in the acute time period following allogeneic organ or tissue transplantation and chronic host-versus-graft rejection.

The phrase "pharmaceutically acceptable", whether used in connection with the pharmaceutical compositions of the invention or vaccine compositions of the invention, refers to molecular entities and compositions that are physiologically tolerable and do not typically produce untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin (18$^{th}$ edition)

The term "about" or "approximately" will be known to those skilled in the art in light of this disclosure. Preferably, the term means within 20%, more preferably within 10%, and more preferably still within 5% of a given value or range. Alternatively, especially in biological systems, the term "about" preferably means within about a log (i.e., an order of magnitude) preferably within a factor of two of a given value, depending on how quantitative the measurement.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins, and may or may not include regulatory DNA sequences, such as promoter sequences, that determine for example the conditions under which the gene is expressed. The transcribed region of a gene can include 5'- and 3'-untranslated regions (UTRs) and introns in addition to the translated (coding) region.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of or "operably associated with" transcriptional and translational control sequences in a cell when RNA polymerase transcribes the coding sequence into mRNA, which is then trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as an mRNA or a protein. The expression product itself, e.g. the resulting mRNA or protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell. "Conditions that permit expression", in vitro are culture conditions of temperature (generally about 37° C.), humidity (humid atmosphere), carbon dioxide concentration to maintain pH (generally about 5% $CO_2$ to about 15% $CO_2$), pH (generally about 7.0 to 8.0, preferably 7.5), and culture fluid components, that depend on host cell type. In vivo, the conditions that permit expression are primarily the health of the non-human transgenic animal, which depends on adequate nutrition, water, habitation, and environmental conditions (light-dark cycle, temperature, humidity, noise level). In either system, expression may depend on a repressor or inducer control system, as well known in the art.

The term "transfection" means the introduction of a "foreign" (i.e. extrinsic or extracellular) gene, DNA or RNA sequence into a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transfected" and is a "transfectant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include plasmids, phages, viruses, etc.; they are discussed in greater detail below.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA segment that can be inserted into a vector or into another piece of DNA at a defined restriction site. Preferably, a cassette is an "expression cassette" in which the DNA is a coding sequence or segment of DNA that codes for an expression product that can be inserted into a vector at defined restriction sites. The cassette restriction sites generally are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid" that generally is a self-contained molecule of double-stranded DNA, usually of bacterial origin, that can readily accept additional (foreign) DNA and which can be readily introduced into a suitable host cell. A plasmid vector often contains coding DNA and promoter DNA and has one or more restriction sites suitable for inserting foreign DNA. A large number of vectors, including plasmid and fungal vectors, have been described for replication and/or expression in a variety of eukaryotic and prokaryotic hosts. Non-limiting examples include pKK plasmids (Amersham Pharmacia Biotech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra. The host cell may be found in vitro, i.e., in tissue culture, or in vivo, i.e., in a microbe, plant or animal.

The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells and Baculovirus vectors, and mammalian host cells and vectors. In a specific embodiment, the protein is expressed in COS-1 or CHO cells. Other suitable cells include NSO cells, HeLa cells, 293T (human kidney cells), mouse primary myoblasts, and NIH 3T3 cells.

The term "heterologous" refers to a combination of elements not naturally occurring. For example, heterologous DNA refers to DNA not naturally located in the cell, or in a chromosomal site of the cell. A heterologous expression regulatory element is such an element operatively associated with a different gene than the one it is operatively associated with in nature. In the context of the present invention, a protein coding sequence is heterologous to the vector DNA in which it is inserted for cloning or expression, and it is heterologous to a host cell containing such a vector, in which it is expressed, e.g., a CHO cell.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization*, B. D. Hames & S. J. Higgins eds. (1985); *Transcription And Translation*, B. D. Hames & S. J.

Higgins, eds. (1984); *Animal Cell Culture*, R. I. Freshney, ed. (1986); *Immobilized Cells And Enzymes*, IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994).

Methods of Producing Antibody Molecules

The antibody molecules of this invention can be produced by any method known in the art for the synthesis of immunoglobulins, in particular, by chemical synthesis or by recombinant expression. Such an isolated nucleic acid that contains a nucleotide sequence encoding the antibody molecule can be produced using any method known in the art. Antibody fragments, such as Fab and F[ab']2, may be produced by proteolytic treatment of whole antibodies.

Various procedures known in the art may be used for the production of polyclonal antibodies to CD99/HEC2 or derivative or analog thereof. For the production of antibody, various host animals can be immunized by injection with the CD99/HEC2 polypeptide, or a derivative (e.g., fragment or fusion protein) thereof, including but not limited to rabbits, mice, rats, sheep, goats, etc. In one embodiment, the CD99/HEC2 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the CD99/HEC2 polypeptide, or fragment, analog, or derivative thereof, any technique that provides for the production of antibody molecules by continuous cell lines in culture may be used. These include but are not limited to the hybridoma technique originally developed by Kohler and Milstein (Nature 1975, 256:495-497), as well as the trioma technique, the human B-cell hybridoma technique (Kozbor et al., Immunology Today 1983, 4:72; Cote et al., Proc. Natl. Acad. Sci. USA 1983, 80:2026-2030), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (PCT Publication No. WO 89/12690). In fact, according to the invention, techniques developed for the production of "chimeric antibodies" (Morrison et al., J. Bacteriol., 1984, 159:870: Neuberger et al., Nature 1984, 312:604-608; Takeda et al., Nature 1985, 314:452-454) by splicing the genes from a mouse antibody molecule specific for an CD99/HEC2 polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. Nos. 5,476, 786, 5,132,405, and 4,946,778) can be adapted to produce CD99/HEC2 polypeptide-specific single chain antibodies. Indeed, these genes can be delivered for expression in vivo. An additional embodiment of the invention utilizes the techniques described for the construction of Fab expression libraries (Huse et al., Science 1989, 246:1275-1281) to allow rapid and easy identification of monoclonal Fab fragments with the desired specificity for a CD99/HEC2 polypeptide, or its derivatives, or analogs.

CD99/HEC2 Polypeptide Expression

Once a nucleic acid containing a nucleotide sequence encoding at least a ligand-binding portion of CD99/HEC2 has been cloned, then the coding sequence can be inserted into a recombinant expression vector. Such engineering of the coding sequence can be accomplished by routine recombinant DNA techniques known in the art.

The nucleic acid encoding the polypeptide optionally contains a nucleotide sequence encoding a leader sequence that directs the secretion of the protein molecule. In the specific case of CD99, which is a transmembrane glycoprotein, a secreted form would be engineered to encode only the extracellular portion, or limited region(s) of the extracellular portion, in order to ensure secretion.

The expression vector can then be transferred to a host cell in vitro or in vivo by conventional techniques and the transfected cells can be cultured by conventional techniques to produce CD99/HEC2. For example, by transient transfection of the expression vector encoding CD99/HEC2 into COS cells, culturing the cells for an appropriate period of time to permit expression, and then taking the supernatant from the COS cells, which supernatant contains the secreted, expressed CD99/HEC2.

The host cells used to express CD99/HEC2 may be either bacterial cells such as *Escherichia coli* or eukaryotic cells. In particular, mammalian cells such as Chinese hamster ovary cells (CHO) or COS cells, used in conjunction with a vector in which expression of CD99/HEC2 is under control of the major intermediate early gene promoter element from human cytomegalovirus is an effective expression system.

A variety of host-expression vector systems may be utilized to express CD99/HEC2. Such host-expression systems represent vehicles by which the coding sequences of interest may be produced and subsequently purified, but also produce cells which may, when transformed or transfected with the appropriate nucleotide coding sequences, exhibit CD99/HEC2 in situ. These systems include, but are not limited to, microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing CD99/HEC2 coding sequences; insect cell systems infected with recombinant virus expression vectors (e.g., baculovirus) containing the CD99/HEC2 coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing CD99/HEC2 coding sequences; mammalian cell systems (e.g., COS, CHO, BHK, 293, and 3T3 cells) harboring recombinant expression constructs containing promoters derived from the genome of mammalian cells (e.g., the metallothionein promoter) or from mammalian viruses (e.g., the adenovirus late promoter; the vaccinia virus 7.5K promoter).

Expression of the protein or polypeptide may be controlled by any promoter/enhancer element known in the art, but these regulatory elements must be functional in the host selected for expression. Promoters that may be used to control gene expression include, but are not limited to, cytomegalovirus (CMV) promoter (U.S. Pat. Nos. 5,385,839 and 5,168,062), the SV40 early promoter region (Benoist and Chambon, Nature 1981, 290:304-310), the promoter contained in the 3' long terminal repeat of Rous sarcoma virus (Yamamoto, et al., Cell 1980, 22:787-797), the herpes thymidine kinase promoter (Wagner et al., Proc. Natl. Acad. Sci. USA, 1981, 78:1441-1445), the regulatory sequences of the metallothionein gene (Brinster et al., Nature 1982, 296:39-42); prokaryotic expression vectors such as the β-lactamase promoter (Villa-Komaroff, et al., Proc. Natl. Acad. Sci. USA, 1978, 75:3727-3731), or the tac promoter (DeBoer, et al., Proc. Natl. Acad. Sci. USA, 1983, 80:21-25); see also "Useful proteins from recombinant bacteria" in Scientific American 1980, 242:74-94; promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Mogram et al., Nature 1985, 315:338-340; Kollias et al., Cell 1986, 46:89-94), hematopoietic stem cell differentiation factor promoters, erythropoietin receptor promoter (Maouche et al., Blood 1991, 15:2557), etc.

In bacterial systems, a number of expression vectors may be advantageously selected depending upon the use intended for the CD99/HEC2 being expressed. For example, when a large quantity of such a protein is to be produced, for the generation of pharmaceutical compositions of CD99/HEC2, vectors which direct the expression of high levels of fusion protein products that are readily purified may be desirable. Such vectors include, but are not limited to, the *E. coli* expression vector pUR278 (Ruther et al., EMBO J. 1983, 2:1791), in which the CD99/HEC2 coding sequence may be ligated individually into the vector in frame with the lac Z coding region so that a fusion protein is produced; pIN vectors (Inouye & Inouye, Nucleic Acids Res. 1985, 13:3101-3109; Van Hleeke & Schuster, J. Biol. Chem. 1989, 264:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The CD99/HEC2 coding sequence may be cloned individually into non-essential regions (for example, the polyhedrin gene) of the virus and placed under control of an AcNPV promoter (for example, the polyhedrin promoter).

In mammalian host cells, a number of viral-based and non-viral-based expression systems may be utilized. In cases where an adenovirus is used as an expression vector, the CD99/HEC2 coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody in infected hosts (see, e.g., Logan & Shenk, Proc. Natl. Acad. Sci. USA, 1984, 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 1987, 153:516-544).

Additionally, a host cell strain may be chosen that modulates the expression of the inserted sequences, or modifies and processes the gene product in the specific fashion desired. Different host cells have characteristics and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38.

For long-term, high-yield production of recombinant proteins, stable expression is preferred. For example, cell lines that stably express CD99/HEC2 may be engineered. Rather than using expression vectors that contain viral origins of replication, host cells can be transformed with DNA controlled by appropriate expression control elements (e.g., promoter, enhancer sequences, transcription terminators, polyadenylation sites, etc.) and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the antibody. Such engineered cell lines may be particularly useful in screening and evaluation of compounds that interact directly or indirectly with the antibody.

A number of selection systems may be used, including but not limited to the herpes simplex virus thyrmidine kinase (Wigler et al., Cell 1977, 11:223), hypoxanthine-guanine phosphoribosyltransferase (Szybalska & Szybalski, Proc. Natl. Acad. Sci. USA 1962, 48:2026), and adenine phosphoribosyitransferase (Lowy et al., Cell 1980, 22:817) genes can be employed in tk-, hgprt-, or aprt-cells, respectively. Also, antimetabolite resistance can be used as the basis of selection for the following genes: dhfr, which confers resistance to methotrexate (Wigler et al., Proc. Natl. Acad. Sci. USA 1980, 77:3567; O'Hare et al. Proc. Natl. Acad. Sci. USA 1981, 78:1527); gpt, which confers resistance to mycophenolic acid (Mulligan & Berg, Proc. Natl. Acad. Sci. USA 1981, 78:2072); neo, which confers resistance to the aminoglycoside G-418 (Colberre-Garapin et al., J. Mol. Biol. 1981, 150:1); and hygro, which confers resistance to hygromycin (Santerre et al., Gene 1984, 30:147).

The expression levels of CD99/HEC2 can be increased by vector amplification (for a review, see Bebbington and Hentschel, The Use of Vectors Based on Gene Amplification for the Expression of Cloned Genes in Mammalian Cells in DNA Cloning, Vol. 3., Academic Press. New York, 1987). When a marker in the vector system expressing CD99/HEC2 is amplifiable, increases in the level of inhibitor present in the culture medium of the host cell will increase the number of copies of the marker gene. Since the amplified region is associated with the CD99/HEC2 gene, production of the protein will also increase (Crouse et al., Mol. Cell. Biol. 1983, 3:257).

Viral and Non-Viral Vectors

Useful vectors in vitro and in vivo are viral vectors, such as lentiviruses, retroviruses, herpes viruses, adenoviruses, adeno-associated viruses, vaccinia virus, alphavirus, baculovirus, and other recombinant viruses with desirable cellular tropism. Thus, a gene encoding a functional or mutant protein or polypeptide domain fragment thereof can be introduced in vivo, ex vivo, or in vitro using a viral vector or through direct introduction of DNA. Expression in targeted tissues can be affected by targeting the transgenic vector to specific cells, such as with a viral vector or a receptor ligand, or by using a tissue-specific promoter, or both. Targeted gene delivery is described in PCT Publication No. WO 95/28494.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques 1992, 7:980-990). Preferably, the viral vectors are replication-defective, that is, they are unable to replicate autonomously in the target cell. Preferably, the replication defective virus is a minimal virus, i.e., it retains only the sequences of its genome which are necessary for encapsidating the genome to produce viral particles.

DNA viral vectors include an attenuated or defective DNA virus, such as but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 1991, 2:320-330), defective herpes virus vector lacking a glyco-protein L gene, or other defective herpes virus vectors (PCT Publication Nos. WO 94/21807 and WO 92/05263); an attenuated adenovirus vector, such as the vector described by Stratford-Perricaudet et al. (J. Clin. Invest. 1992, 90:626-630; see also La Salle et al., Science 1993, 259:988-990); a defective adeno-associated virus vector (Samulski et al., J. Virol. 1987, 61:3096-3101; Samulski et al., J. Virol. 1989, 63:3822-3828; Lebkowski et al., Mol. Cell. Biol., 1988, 8:3988-3996); and a Sindbis virus (a type of alphavirus) (PCT Publication No. WO 98/06237; U.S. Pat. No. 5,091,309).

Various companies produce viral vectors commercially, including, but not limited to, Avigen, Inc. (Alameda, Calif.; AAV vectors), Cell Genesys (Foster City, Calif.: retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

In another embodiment, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner, et. al., Proc. Natl. Acad. Sci. USA, 1987, 84:7413-7417; Felgner and Ringold, Science 1989, 337:387-388; see Mackey, et al., Proc. Natl. Acad. Sci. USA, 1988, 85:8027-8031; Ulmer et al., Science 1993, 259:1745-1748). Useful lipid compounds and compositions for transfer of nucleic acids are described in PCT Patent Publication Nos. WO 95/18863 and WO 96/17823, and in U.S. Pat. No. 5,459,127. Lipids may be chemically coupled to other molecules for the purpose of targeting (see Mackey, et. al., supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., PCT Patent Publication No. WO 95/21931), peptides derived from DNA binding proteins (e.g., PCT Patent Publication No. WO 96/25508), or a cationic polymer (e.g., PCT Patent Publication No. WO 95/21931).

It is also possible to introduce the vector in vivo as a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (see, e.g., Wu et al., J. Biol. Chem. 1992, 267:963-967; Wu and Wu, J. Biol. Chem. 1988, 263:14621-14624; Canadian Patent Application No. 2,012,311; Williams et al., Proc. Natl. Acad. Sci. USA 1991, 88:2726-2730). Receptor-mediated DNA delivery approaches can also be used (Curiel et al., Hum. Gene Ther. 1992, 3:147-154; Wu and Wu, J. Biol. Chem. 1987, 262:4429-4432). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir et al., C.P. Acad. Sci. 1988, 321:893; PCT Publication Nos. WO 99/01157; WO 99/01158; WO 99/01175).

Therapeutic Use of CD99/HEC2 Inhibitors

The invention also provides methods for treating or preventing diseases and disorders associated with CD99-dependent transendothelial migration, e.g., any one or more of the inflammatory conditions disclosed above, by administration of a therapeutic of the invention. Such therapeutics include the aforementioned antibody molecules, small molecules, oligopeptides, proteins, including soluble non-membrane bound CD99/HEC2, and combinations thereof.

Generally, administration of products of a species origin or species reactivity that is the same species as that of the subject is preferred. Thus, in administration to humans, the therapeutic methods of the invention use an antibody molecule that is preferably derived from a human antibody but may be an antibody from a heterologous species such as, for example, a mouse, which may or may not be humanized To enhance the efficacy of the therapeutics contained in the invention, these treatments may be administered in conjunction with other therapies which block the function of other molecules involved in the transendothelial migration of leukocytes. Molecules, other than CD99, involved in leukocyte transendothelial migration, may include PECAM.

The subjects to which the present invention is applicable may be any mammalian or vertebrate species, which include, but are not limited to, cows, horses, sheep, pigs, fowl (e.g., chickens), goats, cats, dogs, hamsters, mice, rats, monkeys, rabbits, chimpanzees, and humans. In a preferred embodiment, the subject is a human.

Gene Therapy

In a specific embodiment, vectors comprising a sequence encoding a protein, including, but not limited to, an antibody molecule, as described, or CD99/HEC2, are administered to treat or prevent a disease or disorder associated with the function of CD99 in the transendothelial migration of leukocytes. In a specific embodiment of this invention, CD99/HEC2 or the above described antibody molecules, are expressed in the blood stream of the patient in a soluble, non-membrane bound form. Soluble CD99/HEC2 or antibody molecules bind to the CD99/HEC2 located in the membranes of leukoctyes or endothelial cells, thereby preventing the intercellular binding of these two cell-types and inhibiting CD99-mediated leukoctye transendothelial migration.

In this embodiment of the invention, the therapeutic vector encodes a sequence that produces, extracellularly (with a leader sequence), a protein of the invention.

Any of the methods for gene therapy available in the art can be used according to the present invention. Exemplary methods are described below.

For general reviews of the methods of gene therapy, see, Goldspiel et al., Clinical Pharmacy 1993, 12:488-505; Wu and Wu, Biotherapy 1991, 3:87-95; Tolstoshev, Ann. Rev. Pharmacol. Toxicol. 1993, 32:573-596; Mulligan, Science 1993, 260:926-932; and Morgan and Anderson, Ann. Rev. Biochem. 1993, 62:191-217; May, TIBTECH 1993, 11:155-215). Methods commonly known in the art of recombinant DNA technology that can be used are described in Ausubel et al., (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13. Dracopoli et al., (eds.), 1994, Current Protocols in Human Genetics, John Wiley & Sons, NY. Vectors suitable for gene therapy are described above.

In one aspect, the therapeutic vector comprises a nucleic acid that expresses a protein of the invention in a suitable host. In particular, such a vector has a promoter operationally linked to the coding sequence for the protein. The promoter can be inducible or constitutive and, optionally, tissue-specific. In another embodiment, a nucleic acid molecule is used in which the protein coding sequences and any other desired sequences are flanked by regions that promote homologous recombination at a desired site in the genome, thus providing for intrachromosomal expression of the protein (Koller and Smithies, Proc. Natl. Acad. Sci. USA 1989, 86:8932-8935; Zijlstra et al., Nature 1989, 342:435-438).

Delivery of the vector into a patient may be either direct, in which case the patient is directly exposed to the vector or a delivery complex, or indirect, in which case, cells are first transformed with the vector in vitro then transplanted into the patient. These two approaches are known, respectively, as in vivo and ex vivo gene therapy.

In a specific embodiment, the vector is directly administered in vivo, where it enters the cells of the organism and mediates expression of the protein. This can be accomplished by any of numerous methods known in the art, e.g., by constructing it as part of an appropriate expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont); or coating with lipids or cell-surface receptors or transfecting agents, encapsulation in biopolymers (e.g., poly-S-1-64-N-acetylglucosamine polysaccharide; see, U.S. Pat. No. 5,635,493), encapsulation in liposomes, microparticles, or microcapsules; by administering it in linkage to a peptide or other ligand known to enter the nucleus; or by administering it in linkage to a ligand subject to receptor-mediated endocytosis (see, e.g. Wu and Wu, J. Biol. Chem. 1987, 62:4429-4432), etc. In another embodiment, a nucleic acid ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publication Nos. WO 92/06180, WO 92/22635, WO 92/20316 and WO 93/14188). Alternatively, the nucleic acid can be introduced intracellularly and incorporated within host cell DNA for expression by homologous recombination (Koller and Smithies, Proc. Natl. Acad. Sci. USA 1989, 86:8932-8935; Zijlstra, et al., Nature, 1989, 342:435-438). These methods are in addition to those discussed above in conjunction with "Viral and Non-viral Vectors".

Alternatively, antibody molecules can also be administered, for example, by expressing nucleotide sequences encoding single-chain antibodies within the target cell population by utilizing, for example, techniques such as those described in Marasco et al. Proc. Natl. Acad Sci. USA, 1993, 90:7889-7893).

The form and amount of therapeutic nucleic acid envisioned for use depends on the type of disease and the severity of the desired effect, patient state, etc., and can be determined by one skilled in the art.

Formulations and Administration

Therapeutic compositions for use in accordance with the present invention can be formulated in any conventional manner using one or more physiologically acceptable carriers or excipients.

Thus, proteins of this invention or nucleic acids encoding them and their physiologically acceptable salts and solvents can be formulated for administration by inhalation (pulmonary) or insufflation (either through the mouth or the nose), by transdermal delivery, or by transmucosal administration, including, but not limited to, oral, buccal, nasal, opthalmic, vaginal, or rectal administration.

For oral administration, the therapeutics can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups, emulsions or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the therapeutics can take the form of tablets or lozenges formulated in conventional manner.

For administration by inhalation, the therapeutics according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The therapeutics can be formulated for parenteral administration (e.g., intravenous, intramuscular, subcutaneous, intradermal) by injection, via, for example, bolus injection or continuous infusion. Formulations for injection can be presented in unit dosage form, e.g., in vials or ampules or in multi-dose containers, with an added preservative. The compositions can take such forms as excipients, suspensions, solutions or emulsions in oily or aqueous vehicles, and can contain formulatory agents such as suspending, stabilizing and/or dispersing agents. Alternatively, the active ingredient can be in dry, lyophilized (i.e. freeze dried) powder form for constitution with a suitable vehicle, e.g., sterile pyrogen-free water or saline, before use.

The therapeutics can also be formulated in rectal compositions such as suppositories or retention enemas, e.g., containing conventional suppository bases such as cocoa butter or other glycerides.

In addition to the formulations described previously, the therapeutics can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Proteins of the invention can be delivered in poly-glycolic acid/lactic acid (PGLA) microspheres (see U.S. Pat. Nos. 5,100,669 and 4,849,222; PCT Publication Nos. WO 95/11010 and WO 93/07861).

The proteins of the invention may be administered as separate compositions or as a single composition with more than one antibody linked by conventional chemical or by molecular biological methods. Additionally, the diagnostic and therapeutic value of the antibodies of the invention may be augmented by their use in combination with radionuclides or with toxins such as ricin or with chemotherapeutic agents such as methotrexate.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the ingredients are supplied either separately or mixed together in unit dosage form, for example, as a dry lyophilized powder or water-free concentrate in a sealed container such as an ampule or sachette indicating the quantity of active agent. Where the composition is administered by injection, an ampule of sterile diluent can be provided so that the ingredients may be mixed prior to administration.

The invention also provides a pharmaceutical pack or kit comprising one or more containers filled with one or more of the ingredients of the formulations of the invention. Associated with such container(s) can be a notice in the form prescribed by a governmental agency regulating the manufacture, use or sale of pharmaceuticals or biological products, which notice reflects approval by the agency of manufacture, use or sale for human administration.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Composition comprising a compound of the invention formulated in a compatible pharmaceutical carrier may also be prepared, placed in an appropriate container, and labelled for treatment of an indicated condition.

Many methods may be used to introduce the formulations of the invention; these include but are not limited to oral, intracerebral, intradermal, intramuscular, intraperitoneal, intravenous, subcutaneous, intranasal routes, and via scarification (scratching through the top layers of skin, e.g., using a bifurcated needle) or any other standard routes of administration Effective Dose The compounds and vectors described herein can be administered to a patient at therapeutically effective doses to treat certain diseases or disorders. A therapeutically effective dose refers to that amount of a therapeutic sufficient to result in a healthful benefit in the treated subject.

The precise dose of the therapeutic embodied by this invention, to be employed in the formulation, will depend on the route of administration, and the nature of the patient's disease, and should be decided according to the judgment of the practitioner and each patient's circumstances according to standard clinical techniques. The term "inhibit" or "inhibition" means to reduce by a measurable amount. The ability of a therapeutic composition or vaccine of the invention to produce this effect can be detected in vitro, e.g., using a transendothelial migration assay as previously described. Further experimental evidence of inhibition includes observing inhibition of inflammation in vivo in an animal model. Effective doses may thus be extrapolated from dose-response curves derived from animal model test systems.

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutics that exhibit large therapeutic indices are preferred. While therapeutics that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$) (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In Vitro Transmigration Assays

In a typical "transmigration assay" in tissue culture inserts, leukocytes are placed in suspension above an endothelial monolayer growing on a porous filter above a lower well of endogenous [made by the endothelium] or exogenous chemoattractant. The leukocytes that end up in the bottom chamber at the end of the assay are counted as transmigrated, and reagents that reduce their number are said to block transmigration. However, in order to get there, the leukocyte must bind to the endothelium, crawl to the nearby junction, diapedese across the endothelium, migrate through the subendothelial basal lamina, crawl through the filter support [usually many times thicker than the endothelium itself], and detach from the underside of the filter. Any reagent that blocks any step in this process would be considered to block transmigration.

Figure 2:
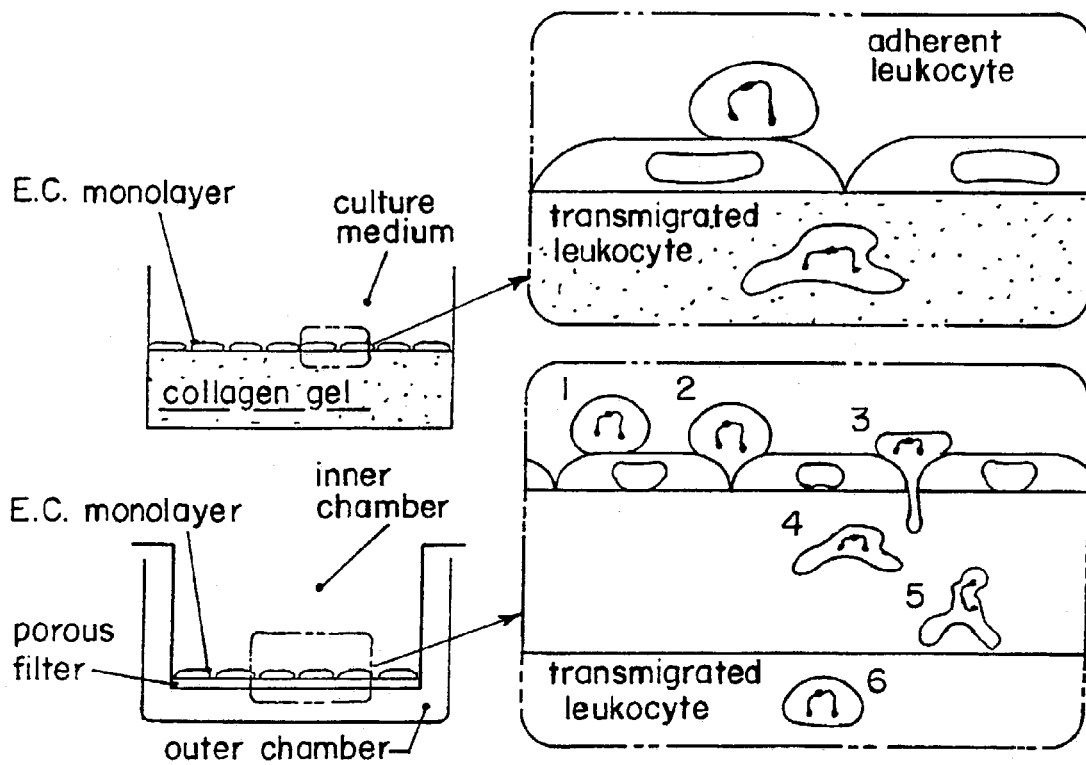
FIG. 2 is a schematic drawing of two in vitro assays of transendothelial migration.

FIG. 2 shows a schematic diagram of two in vitro assays of transendothelial migration (not drawn to scale). As shown in the upper panel, endothalial cells (E.C.) are cultured on hydrated Type I collagen gels overlaid with fibronectin. Components of the culture medium penetrate into the porous gel. The lower panel shows E.C. grown on the upper surface of a porous filter suspended in a larger culture vessel. Culture medium is placed in the inner and outer chambers to reach the apical and basal surfaces of the monolayer, respectively. In the preferred collagen gel method, adherent leukocytes remaining on the apical surface can be distinguished visually from those that have transmigrated. Procedures have also been devised to strip off any leukocytes remaining bound to the apical surface of the monolayer. In the filter chamber method the percentage of the leukocytes added to the upper chamber that appear in the lower chamber is calculated by direct counting. However, in order to be counted as "transmigrated", a leukocyte must 1] attach to the apical surface of the endothelium, 2] migrate to the intercellular junction, 3] diapedese between the endothelial cells, 4] detach from the endothelial cells and penetrate their basal lamina, 5] crawl through the filter itself, and 6] detach from the filter and fall into the chamber below. Reagents that block any of these steps will therefore block the readout of transmigration in this system.

The preferred transmigration assay for use in accordance with this invention (i.e., the upper one) specifically distinguishes apical adhesion from transmigration (1,45), and can even detect a block of transmigrated cells at the level of the subendothelial basal lamina (4).

Transendothelial Migration Assays

All HUVEC, PMN, Mo, and NK cells express PECAM in a unimodal distribution (5,6,11,45). We have been unable to distinguish by surface markers or morphology any difference between those leukocytes that are blocked by anti-PECAM reagents and those that are not. Therefore, functional assays are used to uncover a role for alternative molecules in vivo. HUVEC are cultured on hydrated collagen gels in Medium 199+20% normal human serum, as described (48) and the transendothelial migration assay is preferably run as previously published (1,45). Migration of monocytes can be run in the presence or absence of cytokine stimulation of the endothelium. For experiments to study TEM of neutrophils, the HUVEC monolayer is activated by adding 3 I.U./ml of IL-1β to the culture medium for four hours prior to the assay.

Briefly, monocytes or neutrophils, freshly isolated from venous blood of healthy donors on Ficoll/Hypaque gradients, are allowed to settle on confluent HUVEC monolayers at 37° C. in the presence or absence of test reagents. Preferably the assays are run in Medium 199+0.1% human serum albumin, but there is no difference when run in complete medium (45). After sufficient time for TEM of the control group [generally 1 hour], the monolayers are washed vigorously with 1 mM EGTA to remove any leukocytes still adherent by divalent cation-dependent interactions [selectins or integrins] then rinsed in phosphate buffered saline with divalent cations and fixed in 2.5% glutaraldehyde overnight. This strengthens the collagen gel so that it is easier to manipulate when removed from the 96-well tray. These monolayers are stained with Wright-Giemsa and mounted on slides for direct observation under Nomarski optics.

Tight adhesion to the apical surface of the endothelial monolayer is the rate-limiting step in leukocyte emigration (45), and upon tight adhesion the emigration process becomes independent of shear stress (56). The absence of fluid shear stress in the culture system is therefore of little physiologic relevance, and predictions made based on this in vitro model have held up in several in vivo models (2,6,8, 9,12). The key to this assay is to observe the leukocytes in situ in relation to the confluent endothelial cell monolayer. Using Nomarski optics, one can distinguish by the plane of focus, leukocytes that are attached to the apical surface of the monolayer from those that have transmigrated. One can then quantitate the total number of leukocytes associated with the monolayer visually or by quantitation of fluorescently-labeled leukocytes (1,45) to assess the effect of a reagent on adhesion to the endothelium. Transmigration is quantitated as the percentage of those leukocytes remaining associated with the monolayer that have migrated beneath the monolayer. Therefore, a measurement of TEM is independent of the degree of adhesion to the monolayer and the effects of antibodies or other reagents on adhesion and TEM can be assessed independently.

Obviously, if a leukocyte does not adhere to the endothelial surface, it cannot transmigrate. One could argue, for example, that the population of leukocytes that transmigrates normally in the presence of anti-CD18 might be a separate subpopulation or might be using a different pathway than the "CD18-dependent" leukocytes [that did not bind in the presence of mAb] would have used had they been able to adhere. To address this issue, one may repeat these experiments modifying the procedure as follows: Optimize cytokine activation conditions such that there are multiple adhesion receptors expressed on the endothelial surface [E- and P-selectin, ICAM-1, VCAM-1] such that blocking any particular one does not noticeably affect apical adhesion of the leukocyte population due to the redundancy of adhesion molecules. The TEM assay would be run under these conditions. If adhesion is minimally affected by the presence of the test mAb but TEM is reduced, one could conclude that the molecule in question played a role in TEM that was independent of its role in apical adhesion. Other modifications of the standard TEM assay will be discussed below in reference to particular situations.

The Role of HEC2 in Transendothelial Migration

Which cell bears the critical HEC2? In the experiments infra, the hec2 mAb was present during TEM and thus the results did not distinguish whether the block in TEM was due to hec2 binding to monocytes, endothelium, or both. Purified Fab and F[ab']2 fragments of hec2 selectively prebound to leukocytes or endothelial cells can be used to determine on which cell the antigen is critical. This avoids potential problems with intact Fc-bearing antibody binging to leukocytes via their high affinity Fc receptors, or of turning endothelial cell monolayers into immune complexes and stimulating the adhesion of leukocytes via low affinity Fc receptors to mAb bound to endothelium. Dose-response experiments will determine the optimal blocking concentrations. These experiments are repeated on PMN.

To show that the leukocyte CD99/HEC2 is critical for TEM, monocytes or PMN are incubated in suspension for 30 min at 4° C. with saturating concentrations of Fab fragments of hec2 [as determined by flow cytometry], then washed free of unbound mAb. The leukocytes are added to untreated HUVEC monolayers and the TEM assay run as usual. As a positive control, one could run the TEM assay in the continued presence of optimal concentrations of hec2, conditions known to block TEM. If Fab fragments of hec2 bound to leukocytes alone block TEM as efficiently as Fab added to both cell types simultaneously, we would interpret this to mean that CD99/HEC2 on the leukocyte was critical. This does not rule out a role for endothelial HEC2, however. If hec2 added only to leukocytes blocked TEM very poorly, this would be consistent with the endothelial cell carrying the crucial CD99/HEC2, possibly binding to a different molecule on the leukocyte. If hec2 added to the leukocytes blocked partially, we would suspect that CD99/HEC2 on both leukocytes and endothelial cells was critical, but they bound to different molecules on the apposing cells. No matter what the result, additional experiments test the alternate hypotheses.

To show that the endothelial HEC2 is critical for TEM, confluent HUVEC monolayers are incubated with hec2 Fab or F[ab']2 fragments under conditions determined by immunofluorescence and flow cytometry to produce maximal and saturated staining of HEC2 at the junctions. [For mAb against PECAM and VE-cadherin we have found that 1 hour at 4° C. is sufficient, but this can be located directly.] Unbound mAb are washed away, untreated Mo or PMN are added, and the co-culture warmed to 37° C. for the TEM assay. Again, positive controls are preferably run in the continued presence of optimal concentrations of hec2. If the block in TEM produced when hec2 is added only to endothelial cells is as great as the positive control where both cell types are exposed to the mAb, we would conclude that HEC2 on the endothelial cells is critical. A poor block under these conditions would suggest that HEC2 on the endothelium is not important under these conditions. Again, an intermediate level of block would suggest that both leukocyte and endothelial HEC2 are involved, perhaps binding to different molecules on each other.

The presence of HEC2 on both leukocytes and endothelial cells suggests that HEC2 on the leukocyte may interact in a homophilic way with HEC2 on the endothelium. If optimal blockade of TEM can be achieved by binding the mAb to either leukocyte or endothelial cells, and there is no additive block when mAb is added to both, this would suggest that HEC2 on leukocytes interacts directly with HEC2 on endothelial cells, in a homophilic manner similar to PECAM-1. This can be tested directly with the cloned protein.

There are alternative explanations for an incomplete block in TEM in these experiments. The most common one is endocytosis or destruction of cell-bound mAb during the assay such that it falls to insufficient levels to block TEM. If there is incomplete block when mAb is prebound to cells in the above assays, this possibility can be tested by altering the TEM assay as follows: after prebinding hec2 to the desired cell type, unbound mAb is washed away and the cells are maintained at 4° C. Leukocytes are added to the HUVEC monolayers on ice and allowed to settle in the cold. Under these conditions, antibody is not metabolized as the leukocytes settle on the monolayer surface. In the cold they do not adhere firmly. When the majority of the cells have settled, the culture vessel is warmed rapidly to 37° C. in the incubator and the leukocytes adhere firmly and transmigrate within 5-10 minutes. Immunofluorescence microscopy demonstrates that the vast majority of mAb is still present on the cells at the end of this time. This adaptation of the method allows study of the effects of the added mAb before it is metabolized.

Another explanation for the inability of hec2 to block TEM when added only to one cell type is that the epitope of CD99/HEC2 recognized by mAb hec2 is not the one used by that cell type. For example, if the amino terminus of endothelial HEC2 interacts with an epitope of leukocyte CD99/HEC2 that is close to the membrane, and the hec2 epitope is on the amino terminus of CD99/HEC2, then one would expect that adding hec2 to HUVEC would block TEM, but adding hec2 only to leukocytes would not.

The position of CD99/HEC2 in the order of adhesion events relative to PECAM can also be evaluated. When PECAM function is blocked, leukocytes remain tightly adherent to the endothelium at the cell borders even in the presence of EDTA. This suggests that they are binding by molecules other than the divalent cation-dependent integrin/ICAM interactions. CD99/HEC2 is likely molecule they are attached to. If the leukocytes were bound via CD99/HEC2, they would be released when the blocking mAb is added. This fits with the data in which hec2 partially blocked adhesion of Mo and PMN. If CD99/HEC2 functioned at a step distal to PECAM, there would be no effect of adding mAb at this stage.

To show this, several series of experiments in which leukocytes are first arrested in TEM by anti-PECAM mAb are conducted. In the first series, hec2 or isotype control mAb are subsequently added in the continued presence of anti-PECAM. If bound leukocytes are released, HEC2 is likely the molecule that binds leukocytes in the face of PECAM block. Failure to release leukocytes could be due to a variety of factors. Therefore, a second set of experiments are performed in which, following arrest of TEM by anti-PECAM mAb, the anti-PECAM reagents are washed out and hec2 or control mAb is added. Following washout of anti-PECAM mAb, TEM resumes normally and is complete within 30-90 min (1) in the absence of additional inhibitors. If HEC2 functioned at a step proximal to PECAM, we do not expect to see any blockade, and TEM would be completed normally. However, if HEC2 were involved in a step distal to PECAM, we expect the arrest of TEM to continue.

A third series of experiments can be conducted analogous to the second one in which the order of the application of the mAb would be reversed. Since hec2 significantly blocks adhesion as well as TEM, these experiments are performed under conditions in which apical adhesion molecules are induced by cytokines to hold the leukocytes on to the endothelial surface in the presence of hec2. TEM is first arrested by application of mAb hec2, then anti-PECAM mAb is added after hec2 is washed away. In these experiments anti-PECAM mAb should not prevent subsequent TEM when hec2 is washed away if it functions proximal to HEC2, but should block if PECAM functioned distally. Since leukocytes blocked by anti-PECAM reagents remain tightly adherent to the endothelial cells, repeating the first series of experiments with the order of reagents reversed would not be instructive, but might be performed as an internal control.

Characterization of CD99/HEC2

Clues to the complete function and importance of this molecule come from several straightforward assays (45,48, 57-59). These biochemical and immunological studies complement the data derived from cloning and sequencing the molecule.

Rate of Biosynthesis and Turnover of this Protein

In pulse-chase experiments HUVEC monolayers pre-treated for one hour in methionine- and cysteine-free medium are metabolically labeled with $^{35}$S-methionine and cysteine for one hour followed by a "chase" in nonradioactive medium. At various time points, cells are lysed and immunoprecipitation with hec2 and control mAbs to retrieve the HEC2 and control antigens. These are analyzed by SDS-PAGE and subjected to autoradiography (48). The rate of synthesis and posttranslational modification is determined relative to other markers of the endothelial membrane such as PECAM-1, VE-cadherin [junctional molecules] and ICAM-1 or MHC Class I [diffusely expressed on the plasmalemma] by densitometry of the autoradiograms, or directly by excision of the radioactive bands from the gel (58,59). The rate of turnover can be determined directly in separate experiments in which HUVEC are metabolically labeled to steady state, then radioactive medium is withdrawn. Immunoprecipitation from cell lysates is carried out at time points over two days and analyzed as above for the presence of radioactive HEC2 and control cell markers.

Alternative Forms of CD99/HEC2

Endothelial cells, monocytes, PMN, platelets, and lymphocytes are lysed and probed by Western blot with an anti-CD99/HEC2 antibody, e.g., hec2. This approach has identified a 30 kD molecule by both Western blot and immunoprecipitation of HUVEC. However, HUVEC grown under different conditions [e.g. cytokine stimulation] may express alternatively spliced forms or HEC2 that is glycosylated in a different manner than cells under resting conditions. This finding would suggest that HEC2 had different [or enhanced] functions under these conditions which can be tested directly by running the TEM assay under those cytokine conditions. Leukocytes may express a structurally different molecule that bears the same hec2 epitope. If so, the molecule may have different interactions or signaling pathways on these cell types and more than one cDNA clone.

Association with other Molecules

Under extraction conditions that we employed 0.1% Nonidet P-40 in phosphate buffered saline, followed by washes of the immunoprecipitates in 0.5% NP-40+0.1% SDS, no other molecule co-purified with HEC2 from HUVEC lysates. Immune precipitation from leukocyte or EC lysates under different detergent conditions may reveal an association with other molecules that may transduce signals or link it to the cytoskeleton. These molecules are identified based on reactivity with commercially available antibodies to known signaling and structural molecules, and a first hypothesis about the signal transduction pathways or cytoskeletal elements that HEC2 interacts with will be generated.

Changes in CD99/HEC2 Expression in Response to Inflammatory Cytokines

HEC2's involvement in inflammation suggests this. ICAM-1 expression increases when HUVEC are stimulated by IL-1β or TNFα (45.60). PECAM levels do not increase in the face of cytokine treatment, but IFNγ treatment causes redistribution of PECAM out of the junction toward the apical surface of the cell (61). In a specific assay, Confluent HUVEC monolayers are treated with cytokines relevant to inflammation [e.g. IL-1β, 3-10 I.U./ml for 6 to 24 hours, IFNγ, 100 I.U./ml for 1 to 3 days] and immunofluorescence employed to evaluate for a change in expression or distribution. Known cytokine-responsive adhesion molecules [e.g. ICAM-1 and Class II MHC or PECAM, respectively] can be used as positive controls. Changes in expression level are quantifiable, e.g., by flow cytometry.

Identification of relevant changes in vitro provide evidence that they also occur in situ. Immunoperoxidase histochemistry can be used to determine cellular expression and distribution on vasculature in inflamed tissues from various organs of the human body and compare with its expression on vasculature from matched normal tissues. A wide variety of "waste tissues" for letting are available, e.g., from surgical pathology and autopsy specimens, or skin from patients with psoriasis. Lesional and nonlesional skin from the same person at the same time, and biopsies taken over the course of time, can be compared.

The Mechanism of Action of HEC2

The predicted amino acid sequence of the molecule gives a clue to its potential functions (FIG. 4). "Sequence gazing" provides a starting place for experimentation. The cloned molecule is expressed in a variety of mammalian cells to determine which functions[s] expressing the molecule imparts to these cells, e.g., similar to experiments with the junctional adhesion molecules PECAM (7,49,53,65) and VE-cadherin (29). Of particular importance are soluble forms of CD99/HEC2, i.e., the extracellular domain of ligand binding portion thereof, which can be used as inhibitors of CD99/HEC2 function. In a specific aspect, a CD99-Ig chimeras, analogous to the PECAM-Ig chimeric construct discussed infra, is prepared.

Since adding hec2 to EC delayed formation of confluent monolayers, it is a reasonable hypothesis that HEC2 has adhesive functions. Since it is expressed on both leukocytes and endothelium, one might suspect that it mediates homophilic interactions between these cells. This will be tested in both short term [L cell aggregation assays] and long term [culture] assays as previously described (7,29,49,53, 65).

L cells are a murine fibroblast cell line that show little tendency to spontaneously bind each other. Expression of exogenous adhesion molecules by transfection imparts on them the adhesive properties of those molecules. L cells transfected with HEC2 cDNA are nonenzymatically resuspended by brief incubation in 10 mM EDTA, washed, and resuspended in buffer at 106 cells/ml. One ml of this suspension is placed in each well of a 24-well culture tray and placed on a gyrotory shaker at 90 rpm. At time zero and various time points up to an hour, aggregation is stopped by adding glutaraldehyde to a final concentration of 2%. If L cells expressing HEC2 on their surfaces bind to each other, they will form aggregates that are quantitated in a hemacytometer. The temperature dependence and divalent cation dependency of the adhesion are easily tested in such an assay. Potential inhibitors of the adhesion are added at time zero and their effect on adhesion is quantitated. In particular, mAb hec2, which blocks transmigration of leukocytes should block adhesion.

Since both EC and leukocytes have HEC2, it is reasonable to hypothesize that the adhesion is homophilic. That is, a molecule of HEC2 on one cell binds to a molecule of HEC2 on the apposing cell. In order to test this hypothesis, two populations of L cells are mixed. HEC2 transfectants are mixed in the aggregation assay with an equal number of fluorescently labeled parental cells. At the end of the assay aggregates are examined under the fluorescent microscope. If binding is homophilic, only HEC2 transfectants should be in the aggregates, which would be nonfluorescent. If binding is heterophilic [HEC2 binds to another molecule endogenously expressed on the L cell surface] then mixed aggregates of labeled and unlabeled cells will be seen (65). The assay is then repeated with the labeled populations switched.

These assays demonstrate that CD99-transfected L cells aggregate in a homophilic manner that is divalent cation-dependent and fairly insensitive to temperature over the range of 4°-37° C.

These assays are repeated by mixing HEC2 transfectants with leukocytes or endothelial cells, which putatively contain ligands for HEC2. In this case we would expect that HEC2 transfectants would bind to the leukocytes or endothelial cells in a manner that is blocked by adding hec2 to the transfectants, but not to the leukocytes or EC.

In long-term assays, transfected cells are mixed with nontransfected fibroblasts in culture, which again are distinguished by an exogenous label. The cells are co-cultured for a number of days then stained with hec2 to determine the distribution. If binding is homophilic at the junctions, then HEC2 will be concentrated only at the borders that transfected cells make with each other and not at the borders made with nontransfected cells.

If interaction between the HEC2 on endothelial cells and leukocytes is heterophilic, that raises the possibility that there are unique ligands on leukocytes for endothelial HEC2 and on endothelial cells for leukocyte HEC2. HEC2 ligands on leukocytes and endothelial cells can be identified by mixing HEC2 transfectants with large numbers of radiolabeled leukocytes and ECV-304, respectively. The cells are lysed under mild detergent conditions and the lysates passed over a hec2-Sepharose column. This will bind HEC2 and its attached ligand. The bound material is eluted and run on SDS-PAGE. Radioactive bands represent candidate HEC2 ligands. These bands are cut from the gels and subjected to protein sequencing.

HEC2 Function in TEM

Hec2 mAb blocks at least two functions. Addition of the mAb to subconfluent HUVEC cultures delays the formation of a confluent monolayer. Addition of mAb to leukocyte-endothelial cell co-cultures blocks TEM. Thus, adhesion of the mAb to cells either prevents the interaction of HEC2 with a molecule on the opposite cell [or secreted into solution] or stimulates an action. CD99/HEC2 may act as an adhesion molecule, and/or that it may be responsible for the initial calcium signaling required for TEM. The CD99/HEC2 cDNA clone can be used to confirm these functions.

It is known that a rise in intracellular free calcium in endothelial cells is required for TEM (66). Blocking this rise will inhibit transmigration, but not adhesion of PMN to endothelial cells (66). Fluo3 [Molecular Probes, Eugene, Oreg.], or other $Ca^{++}$-sensitive reagents, can be used determine whether an intracellular calcium flux takes place shortly after leukocyte/EC engagement. In a specific embodiment, confluent HUVEC monolayers are washed free of serum and incubated with Fluo3-AM [3.3 mM solubilized in Pluronic F-127 and DMSO] in heat-inactivated calf serum for 40 min. at room temperature. This diffuses into the cells where cytoplasmic esterases cleave the acetoxy methyl ester, rendering the dye membrane-impermeable. Sulfinpyrazone [0.25 mM] or probenecid [2.5 mM] is added to block organic anion transporters that pump the dye out of the cell and into endosomes (67). A rise in intracellular calcium produces a dramatic increase in fluorescence of Fluo3, which can be quantitated on our Cytofluor® instrument, visualized by fluorescence microscopy, or detected by flow cytometry on the FITC channel.

When leukocytes migrate across these Fluo3-loaded HUVEC monolayers, there is an increase in fluorescence due to an increase in cytosolic free calcium $\{[Ca^{++}]i\}$. This calcium flux may be blocked by hec2 mAb; if so, HEC2 is responsible for generating this signal. HEC2's direct involvement in calcium signaling can be tested by designing conditions in which HEC2 transfectants reproduce the same phenomenon. If homophilic HEC2 interactions between leukocyte and endothelium stimulate the rise in $[Ca^{++}]i$ then cross-linking HEC2 on HUVEC by mAb could stimulate it as well.

Cloning the Murine Equivalent and Making Blocking mAb

The effects of hec2 on TEM of monocytes and PMN in the in vitro assay provides information about the role of HEC2 in TEM. To test this in vivo, blocking antibodies are generated to the murine homologue and HEC2-deficient mice are made. The murine CD99/HEC2 molecule is claimed recombinant protein produced, and this is used to generate monoclonal antibodies, e.g., in rats, rabbits, or hamsters. Alternatively antibodies can be generated against murine CD99/HEC2 peptides from the extracellular domain.

Murine libraries are screened with our full-length human clone, relying on homologous regions to hybridize at reasonable stringency. This is the way murine PECAM-1 was cloned based on the human clone (53).

Polyclonal antibody against human CD99/HEC2 may be generated in rabbits that cross-reacts with murine hec2 antigen. If so, the murine form of the molecule could be cloned using this antibody to screen murine leukocyte or endothelial cell cDNA expression libraries. The murine cDNA clone is sequenced and subcloned into mammalian expression vectors. Transfected cells are subjected to the same assays that identified the functions of the human form to confirm its identity as murine CD99/HEC2, recognizing that ligands and signal transduction pathways might differ among species.

In a specific embodiment stably transfected rat fibroblasts expressing high levels of the murine protein are used to immunize rats of the same MHC class as the fibroblasts. In this way, the main foreign protein on the cells will be murine HEC2. Hybridomas secreting monoclonal antibodies would be generated by fusion of splenic B cells with rat myeloma cells using standard methods (68,69). These are screened by selecting those clones whose supernates bound to the transfected fibroblasts used for immunization but not to parental rat fibroblasts. Immunizing with antigen expressed on cells is a more effective way to make mAb that block function on intact cells than injection of purified antigen in Freund's adjuvant. Hybridomas are tested for their ability to block in vitro functions of the transfected cells as well as to bind to the authentic murine antigen on leukocytes and endothelium. Cloned hybridomas are expanded and purified IgG prepared for in vivo studies.

Transmigration Assays in PECAM Defective Mice

We have recently produced transgenic mice that constitutively express soluble murine PECAM as a dimeric PECAM-IgG chimeric protein. Line $Tg8_{20}$ mice that have circulating concentrations of 20 μg/ml (which corresponds to the levels reached by doses of exogenously administered PECAM-IgG that block inflammation maximally) are healthy in the clean environment of the animal facility, but have a severely blunted acute inflammatory response. They only mobilize 10-20% of the PMN and monocytes that their wild-type littermates do. This suggests that a normal host do not become tolerized to therapeutic levels of this anti-PECAM reagent. These mice are valuable for studying the role of PECAM in chronic inflammation and the effect of chronic interference with PECAM function on the inflammatory response. These mice also demonstrate that expression of an inhibitor of inflammation (i.e., PECAM-IgG) at therapeutic levels does not inhibit basal inflammatory responses such as subclinical wound repair and does not render the mice immunodeficient. Thus, it is likely that therapeutic levels of anti-CD99 reagents could be administered chronically without untoward effects on cells involved in the inflammatory response.

Various laboratories have established that PECAM plays a critical role in the TEM of neutrophils [PMN], monocytes [Mo], and natural killer [NK] cells. Inhibitors of PECAM function block the vast majority of TEM both in vitro (1,4,6,7) and in vivo in several different models (2,8-11). However, even under the most optimal conditions, we have never been able to block TEM more than 80-90% using monoclonal or polyclonal antibodies, soluble PECAM-IgG chimeras, or combinations thereof (4,6). Even the $Tg8_{20}$ transgenic PECAM-IgG mice exposed constitutively to maximally therapeutic concentrations [20 mg/ml] still manage to mobilize 10-20% of their leukocytes in response to an acute inflammatory stimulus. These data suggest that PECAM-independent pathways normally exist and are responsible for this residual leukocyte emigration in the face of maximal PECAM blockade. In some inflammatory conditions, particularly chronic ones, this residual TEM may be enough to produce clinical symptoms in the face of maximally effective anti-PECAM therapy. Therefore, it is important to identify these alternative TEM pathways, determine how they function, and how to best inhibit them.

In a model of acute inflammation in which neutrophil emigration was stimulated by application of the chemotactic peptide formyl-methionyl-leucyl-phenylalanine [fMLP] directly on the mesentery of rats, anti-PECAM antibody did not block PMN extravasation, whereas the same antibody did block PMN extravasation when IL-1β was used to activate the endothelium of mesenteric venules (9). Thus, there is at least one stimulus that will elicit PECAM-independent leukocyte emigration in wild-type animals. Mice homozygous for a targeted deletion of PECAM-1 do not show any significant defects in a variety of acute inflammatory models (26). These mice by definition use alternative mechanisms for TEM.

Anti-PECAM therapy has been demonstrated to block TEM in the mesentery (2,6,8,9) the lung (8), skin (8,11), myocardium (10,12), and probably the cornea (27). However, this leaves open the possibility that in other vascular beds the role of PECAM is less important. Most leukocyte emigration at sites of acute inflammation is across postcapillary venules. In the lung, however, emigration takes place across capillaries. In atherosclerosis and many forms of arteritis, leukocyte emigration takes place across arterial endothelium.

A formidable impediment characterizing CD99/HEC2 in vivo is that in wild-type mice anti-PECAM reagents block transmigration so well. Given the standard errors inherent in animal experiments, when anti-PECAM blocks 85±10% of leukocyte emigration, it may be very difficult to identify a block in the residual ~15%. Two different types of mice have accordingly beem developed to study PECAM-independent pathway[s] of transmigration. In these mice all TEM takes place through PECAM-independent pathways. Mice with a targeted deletion of the PECAM-1 gene have normal leukocyte counts and only a very minor defect in their inflammatory response. These mice have developed in the absence of PECAM, so they must use alternative adhesion molecules for TEM. In addition two independent lines of transgenic mice [$Tg5_{1000}$ and $Tg11_{1000}$] that constitutively express supratherapeutic levels of the soluble PECAM-IgG chimera have been developed, which circulates in their blood at 500 to 2,000 μg/ml. While the transgenic protein they express is perfectly active when transferred to wild-type mice, these mice are paradoxically resistant to its anti-inflammatory effects. Since these mice have normal levels of endogenous PECAM on their leukocytes and endothelial cells, they must be using PECAM-independent pathways for TEM.

The normal inflammatory phenotype of the PECAM "knockouts" suggests that PECAM-independent pathways can be quantitatively expanded to support normal levels of TEM. The results with the $Tg5_{1000}$ and $Tg11_{1000}$ transgenic mice suggests that very high levels of circulating anti-PECAM reagents can desensitize the host over time to its anti-inflammatory effects. These transgenic mice are used to characterize more fully the CD99/HEC2 pathways of TEM.

Screening and Chemistry

According to the present invention, nucleotide sequences derived from the gene encoding CD99/HEC2, and peptide sequences derived from CD99/HEC2, are useful targets to identify drugs that are effective in treating inflammatory conditions. Drug targets include without limitation (i) isolated nucleic acids derived from the gene encoding CD99/HEC2; (ii) isolated peptides and polypeptides derived from CD99/HEC2 polypeptides; isolated peptides and polypeptides derived from CDE99/HEC2 binding partners; carbohydrate groups found on CD99/HEC2; and small molecule mimetics or analogs thereof.

In particular, identification of CD99/HEC2 as an important mediator of TEM provides for development of screening assays, particularly for high throughput screening of molecules that up- or down-regulate the activity of CD99/HEC2. Accordingly, the present invention contemplates methods for identifying specific ligands of CD99/HEC2 using various screening assays known in the art.

Any screening technique known in the art can be used to screen for CD99/HEC2 agonists or antagonists. The present invention contemplates screens for small molecule ligands or ligand analogs and mimics, as well as screens for natural ligands that bind to and agonize or antagonize CD99/HEC2 in vivo. Such agonists or antagonists may, for example, interfere in the adhesion properties or TEM properties of CD99/HEC2, with resulting effects on CD99/HEC2 function. For example, natural products libraries can be screened using assays of the invention for molecules that agonize or antagonize CD99/HEC2 activity.

Knowledge of the primary sequence of CD99/HEC2, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith. Science 1990, 249:386-390; Cwirla, et al., Proc. Natl. Acad. Sci. USA 1990, 87:6378-6382; Devlin et al., Science 1990, 49:404-406), very large libraries can be constructed ($10^6$-$10^8$ chemical entities). A second approach uses primarily chemical methods, of which the Geysen method (Geysen et al., Molecular Immunology 1986, 23:709-715; Geysen et al. J. Immunol. Meth. 1987, 102:259-274; and the method of Fodor et al. (Science 1991, 251:767-773) are examples. Furka et al. (14th International Congress of Biochemistry 1988, Volume #5, Abstract FR:013; Furka, Int. J. Peptide Protein Res. 1991, 37:487-493), Houghton (U.S. Pat. No. 4,631,211) and Rutter et al. (U.S. Pat. No. 5,010,175) describe methods to produce a mixture of peptides that can be tested as agonists or antagonists.

In another aspect, synthetic libraries (Needels et al., Proc. Natl. Acad. Sci. USA 1993, 90:10700-4; Ohlmeyer et al., Proc. Natl. Acad. Sci. USA 1993, 90:10922-10926; PCT Publication Nos. WO 92/00252 and WO 9428028) and the like can be used to screen for CD99/HEC2 ligands according to the present invention.

Test compounds are screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet. Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (NC), or are readily producible. Additionally, natural and synthetically produced libraries and compounds are readily modified through conventional chemical, physical, and biochemical means (Blondelle et al., Tib Tech 1996, 14:60).

In Vitro Screening Methods

Candidate agents are added to in vitro cell cultures of endothelial cells, or to purified CD99/HEC2 (preferably in a stable soluble form, e.g., expressed as a CD99/Ig chimeric construct), and their ability to bind to CD99 (particularly for a primary screen to identify candidate compounds), or more preferably their ability to inhibit binding of leukocytes to CD99/HEC2, is evaluated. In endothelial cell culture systems, the ability to inhibit TEM can be evaluated.

A number of suitable in vitro systems are described above.

In Vivo Screening Methods

Intact cells or whole animals expressing a gene encoding CD99/HEC2 can be used in screening methods to identify and further characterize candidate drugs. Any of the animal models or transgenic animal models described above are suitable for screening of CD99/HEC2 antagonists.

In one series of embodiments, a permanent cell line is established. Alternatively, cells (including without limitation mammalian, insect, yeast, or bacterial cells) are transiently programmed to express an CD99/HEC2 gene by introduction of appropriate DNA or mRNA, e.g., using the vector systems described above. Identification of candidate compounds can be achieved using any suitable assay, including without limitation (i) assays that measure selective binding of test compounds to CD99/HEC2 (ii) assays that measure the ability of a test compound to modify (i.e., inhibit or enhance) a measurable activity or function of CD99/HEC2 and (iii) assays that measure the ability of a compound to modify (i.e., inhibit or enhance) the transcriptional activity of sequences derived from the promoter (i.e., regulatory) regions the CD99/HEC2 gene.

In Vivo Testing Using Transgenic Animals

Transgenic mammals can be prepared for evaluating the molecular mechanisms of CD99/HEC2 as described above. Preferably, for evaluating compounds for use in human therapy, the animals are "humanized" with respect to CD99/HEC2. Such mammals provide excellent models for screening or testing drug candidates. The term "transgenic" usually refers to animal whose germ line and somatic cells contain the transgene of interest, i.e., CD99/HEC2. However, transient transgenic animals can be created by the ex vivo or in vivo introduction of an expression vector of the invention. Both types of "transgenic" animals are contemplated for use in the present invention, e.g., to evaluate the effect of a test compound on CD99/HEC2 activity.

Thus, human CD99/HEC2, or CD99/HEC2 and, or both, "knock-in" mammals can be prepared for evaluating the molecular biology of this system in greater detail than is possible with human subjects. It is also possible to evaluate compounds or diseases on "knockout" animals, e.g., to identify a compound that can compensate for a defect in CD99/HEC2 acitivity. Both technologies permit manipulation of single units of genetic information in their natural position in a cell genome and to examine the results of that manipulation in the background of a terminally differentiated organism.

Although rats and mice, as well as rabbits, are most frequently employed as transgenic animals, particularly for laboratory studies of protein function and gene regulation in vivo, any animal can be employed in the practice of the invention.

A "knock-in" mammal is a mammal in which an endogenous gene is substituted with a heterologous gene (Roemer et al., New Biol. 1991, 3:331). Preferably, the heterologous gene is "knocked-in" to a locus of interest, either the subject of evaluation (in which case the gene may be a reporter gene; see Elefanty et al., Proc. Natl. Acad. Sci. USA 1998, 95:11897) of expression or function of a homologous gene, thereby linking the heterologous gene expression to transcription from the appropriate promoter. This can be achieved by homologous recombination, transposon (Westphal and Leder, Curr. Biol. 1997, 7:530, 1997), using mutant recombination sites (Araki et al., Nucleic Acids Res. 1997, 25:868) or PCR (Zhang and Henderson, Biotechniques 1998, 25:784). See also, Coffman, Semin. Nephrol. 1997, 17:404; Esther et al., Lab. Invest. 1996, 74:953; Murakami et al., Blood Press. Suppl. 1996, 2:36.

A "knockout mammal" is an mammal (e.g., mouse) that contains within its genome a specific gene that has been inactivated by the method of gene targeting (see, e.g., U.S. Pat. Nos. 5,777,195 and 5,616,491). A knockout mammal includes both a heterozygote knockout (i.e., one defective allele and one wild-type allele) and a homozygous mutant. Preparation of a knockout mammal requires first introducing a nucleic acid construct that will be used to suppress expression of a particular gene into an undifferentiated cell type termed an embryonic stem cell. This cell is then injected into a mammalian embryo. A mammalian embryo with an integrated cell is then implanted into a foster mother for the duration of gestation. Zhou, et al. (Genes and Development 1995, 9:2623-34) describes PPCA knock-out mice.

The term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise 1) a full or partial sequence of one or more exons and/or introns of the gene to be suppressed, 2) a full or partial promoter sequence of the gene to be suppressed, or 3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo. However, the invention does not require any particular method for preparing a transgenic animal.

Generally, for homologous recombination, the DNA will be at least about 1 kilobase (kb) in length and preferably 34 kb in length, thereby providing sufficient complementary sequence for recombination when the construct is introduced. Transgenic constructs can be introduced into the genomic DNA of the ES cells, into the male pronucleus of a fertilized oocyte by microinjeciton, or by any methods known in the art, e.g., as described in U.S. Pat. Nos. 4,736,866 and 4,870,009, and by Hogan et al., *Transgenic Animals: A Laboratory Manual,* 1986, Cold Spring Harbor. A transgenic founder animal can be used to breed other transgenic animals; alternatively, a transgenic founder may be cloned to produce other transgenic animals.

Included within the scope of this invention is a mammal in which two or more genes have been knocked out or knocked in, or both. Such mammals can be generated by repeating the procedures set forth herein for generating each knockout construct, or by breeding to mammals, each with a single gene knocked out, to each other, and screening for those with the double knockout genotype.

Regulated knockout animals can be prepared using various systems, such as the tet-repressor system (see U.S. Pat. No. 5,654,168) or the Cre-Lox system (see U.S. Pat. Nos. 4,959,317 and 5,801,030).

High-Throughput Screen

Agents according to the invention may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time. Such high-throughput screening methods are particularly preferred. The use of high-throughput screening assays to test for agents is greatly facilitated by the availability of large amounts of purified polypeptides, as provided by the invention.

EXAMPLES

The present invention will be better understood by reference to the following Examples, which are intended as illustrative of the invention and not limiting thereof.

Example 1

CD99/HEC2: A Novel Molecule Involved in Transendothelial Migration

Using the same strategy that we used to raise mAb against PECAM-1 (48) and VE-cadherin (29) (Example 2), we have raised a murine mAb [hec2] against another human endothelial cell junctional protein. The antigen, temporarily designated HEC2, is expressed at the junctions of confluent human umbilical vein endothelial cell [HUVEC] monolayers. In particular, HEC2 is concentrated at intercellular borders of endothelial cells. Replicate confluent HUVEC monolayers were fixed, permeabilized and stained with mouse mAb against PECAM, VE-cadherin/cadherin 5 [VE-CAD5]. HEC2, or ICAM-1. Binding was visualized using a Cy3-labeled goat anti-mouse antibody. The staining of HEC2 is concentrated at the lateral borders of the endothelial cells, similar to the known junctional molecules, PECAM and VE-cadherin. On the other hand, mAb against the apical surface antigen ICAM-1 produces diffuse surface staining, demonstrating that the concentration of stain at the borders is not an artifact of our staining procedure.

HEC2 is expressed in situ on arterial and venous endothelium of umbilical cord. In skin it is expressed on endothelium of arterioles, capillaries, and venules, as well as stellate macrophages in the dermis. The antigen is not expressed on vascular smooth muscle cells, fibroblasts, keratinocytes, epithelium of eccrine ducts.

Flow cytometric analysis of peripheral blood detected HEC2 on PMN, monocytes and lymphocytes. It is also expressed by the ECV-304 endothelial cell line, platelets, and megakaryocytes. Purified leukocytes and nonenzymatically resuspended ECV-304 cells were incubated with mAb against the indicated antigens, washed, incubated with a FITC-rabbit anti-mouse IgG, and subjected to flow cytometric analysis. Peripheral blood mononuclear cells [PBMC] contain both lymphocytes and monocytes, which were not gated separately. A unimodal staining pattern is seen in each case.

Immune precipitation and Western blotting both reveal a molecule with an apparent molecular weight of 30 kD under both reducing and nonreducing conditions. As such, it does not appear to be any known junctional molecule. The putative human equivalent of JAM migrates as two distinct molecular forms of 38 and 48 kD on the same gel (36). Occludin has a Mr of 60 kD and members of the claudin family have molecular weights of about 22-23 kD. To obtain HEC2 molecular weight data, endothelial cell lysates were separated by SDS-PAGE under non-reducing conditions and subjected to immunoblot analysis in duplicate with mAb against HEC2 or against PECAM. Molecular weight standards were run in lane 3, with the Mr in kilodaltons indicated. The mAb hec2 recognizes a 30 kD molecule.

Resting endothelial cells were metabolically labeled with 35S-methionine and cysteine overnight. Cell lysate was divided and subjected to immune precipitation using mAb against PECAM, Class II MHC [negative control], HEC2, and human junctional adhesion molecule [JAM]. The precipitates were subjected to SDS-PAGE under reducing conditions and analyzed by autoradiography. A molecule running at 30 kD is identified by hec2 mAb.

When hec2 mAb is added to a subconfluent monolayer of HUVEC, it delays the formation of a confluent monolayer. However, it has no effect on the integrity of a monolayer when added to the culture medium after the cells come to confluence. In this regard, it is similar to hec7 and other mAb against PECAM (49,50).

In multiple experiments, hec2 mAb blocked TEM of monocytes by greater than 90% (FIG. 3). Transmigration of PMN was also reduced, but to a lesser degree. This block occurred in the absence of anti-PECAM reagents, indicating that PECAM did not have to be inhibited in order to see the effect of CD99 on TEM. This suggests that PECAM and CD99 function in distinct stages of TEM. When both hec2 and anti-PECAM antibody were combined, transmigration of monocytes was essentially abolished (see, FIG. 3D). The mAb hec2 also blocked adhesion of Mo to EC (FIGS. 2A and 3B). However, the block in TEM was a distinct, separate, and quantitavely greater phenomenon.

As shown in FIG. 3, CD99/HEC2 and CD11/CD18 play novel roles in transendothelial migration of monocytes. Moncytes were incubated with resting HUVEC monolayers and TEM assays run by our standard procedures. In these assays mAb [10 mg/ml] was present during the time of co-culture so that both cell types were exposed to it. Monolayers were then washed extensively before counting total cells [adhesion, cells/high powered field] and percent of remaining cells that transmigrated [% transmigration]. mAb against CD18 blocks adhesion significantly, as does mAb against ICAM-1 and HEC2 (FIG. 3A). Note that mAb against PECAM has no effect on adhesion of Mo. When the indicated antibodies were each combined with anti-PECAM mAb at 10 mg/ml anti-CD18 does not block adhesion any better (FIG. 3B). The combination of mAb against ICAM-1 and mAb against ICAM-2 [ICAM 1+2] blocks adhesion almost as well as anti-CD18.

Figure 3A:
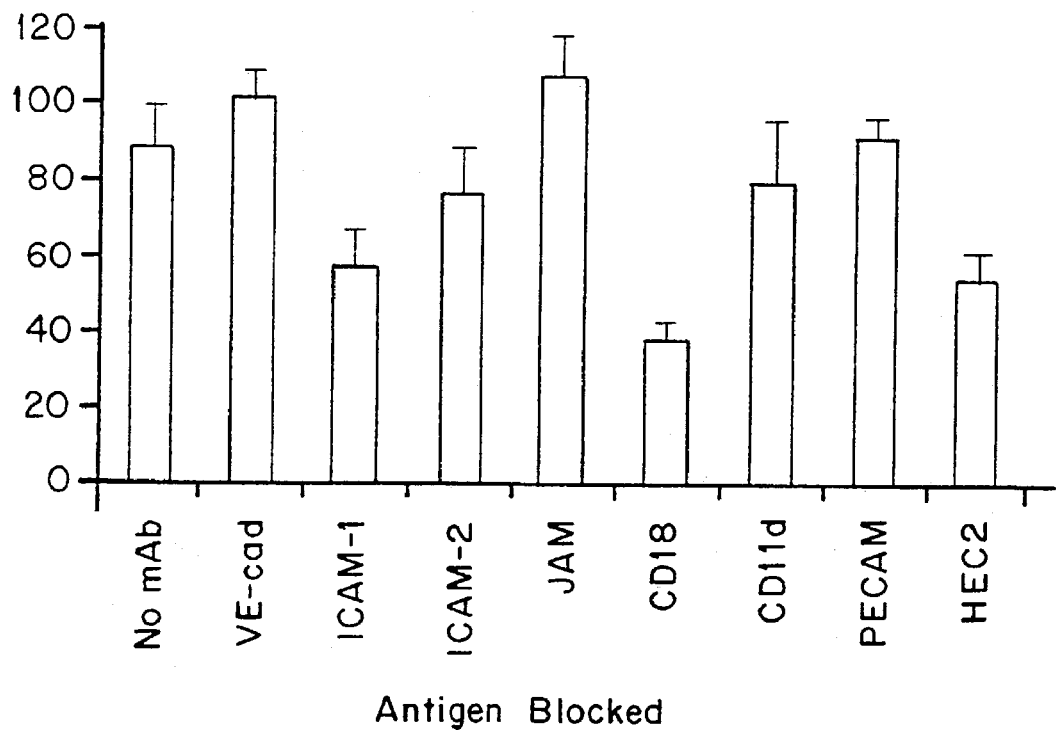
FIG. 3 shows experimental data indicating the effect of blocking various antigens, with antibodies, on cellular adhesion and transendothelial migration.
Figure 3B:
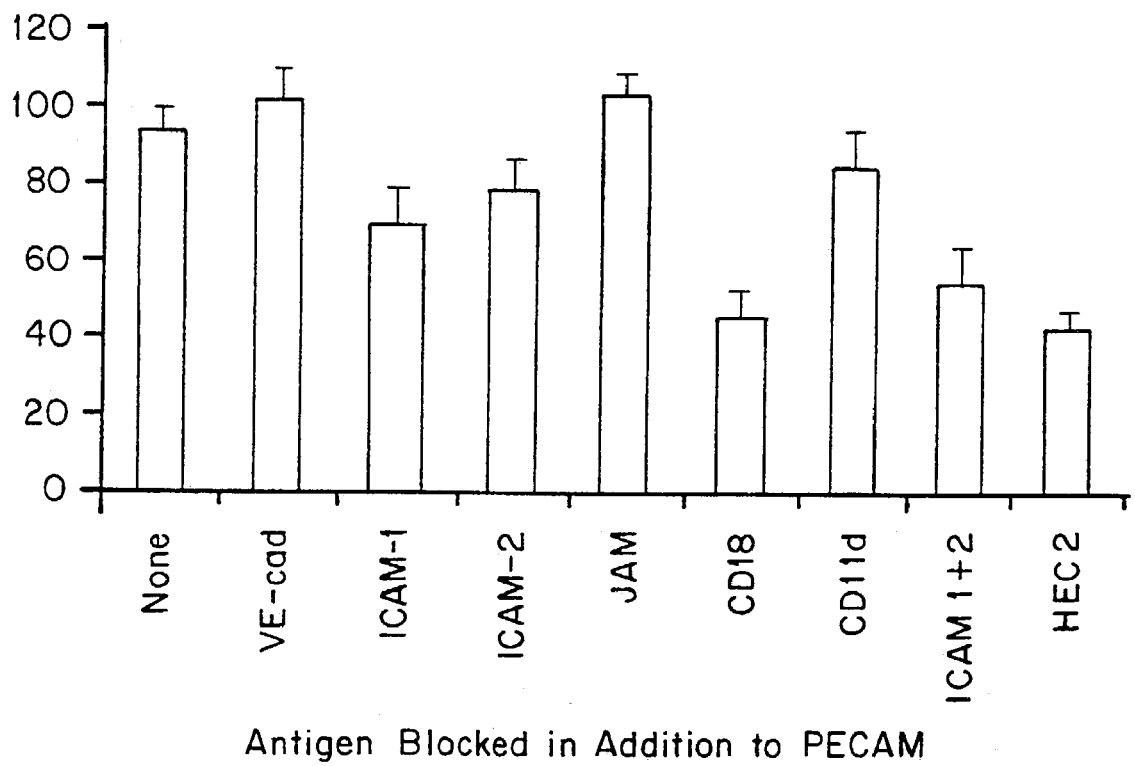
Figure 3C:
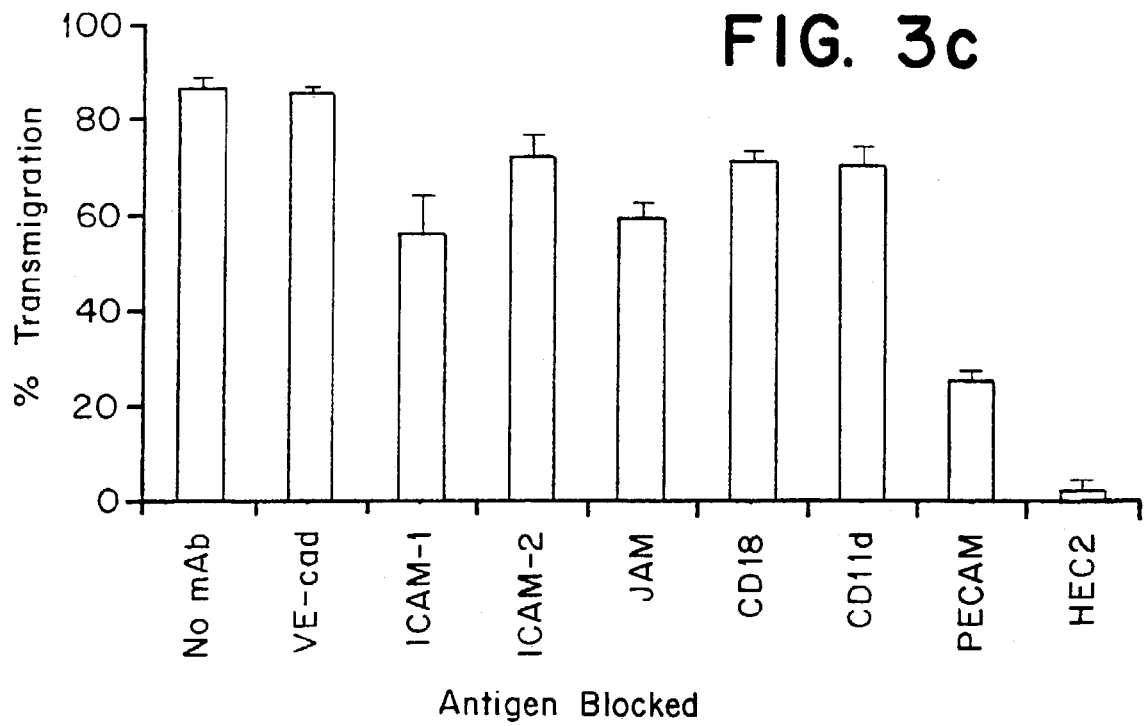
Figure 3D:
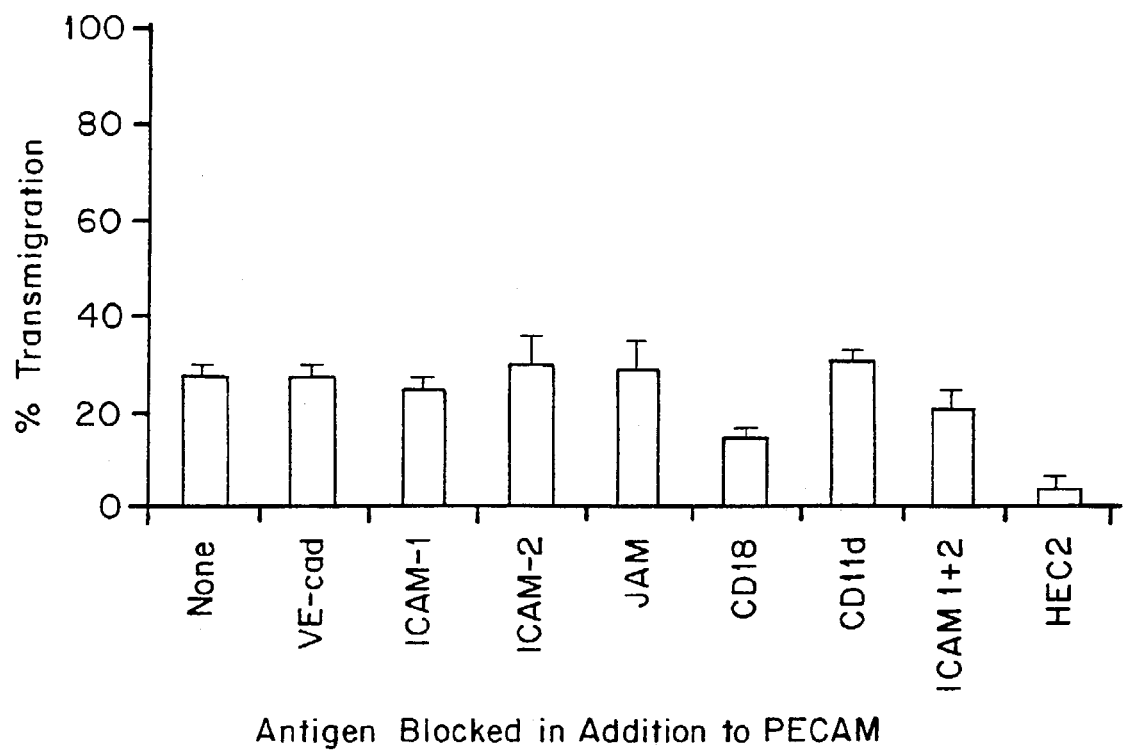
Figure 5:
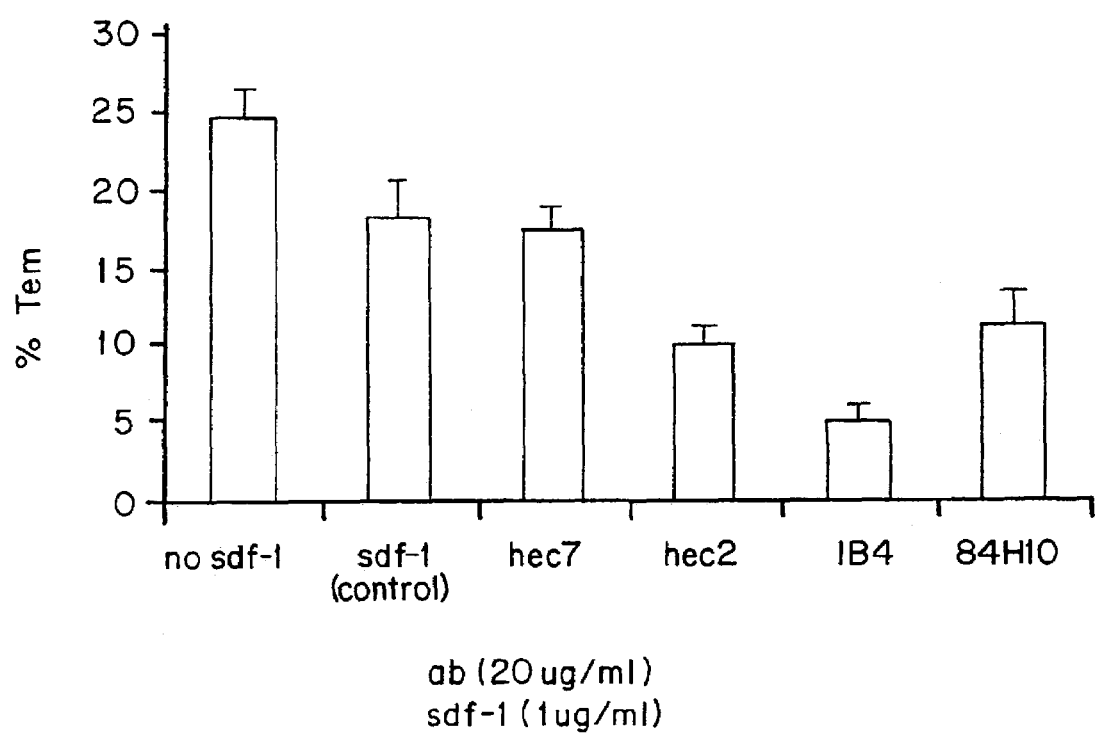
FIG. 5 is a graph showing percent of T cell migration through a HUVEC monolayer on collagen gel.

The percentage of the cells remaining with the monolayer that transmigrated was significantly reduced by mAb against PECAM and HEC2, but by no other mAb (FIG. 3C). When mAb were combined with anti-PECAM mAb, the combination of anti-PECAM and anti-HEC2 blocks TEM almost completely (FIG. 3D). Numbers shown are mean±S.E.M. of 5 to 27 replicates from 2 to 7 experiments with each mAb. A block was considered significant if $p<0.05$, but in most cases it was $<0.01$.

Example 2

Generation of the hec2 Monoclonal Antibody

Monoclonal antibody hec2 was prepared according to the following methods.

Isolation of Human Umbilical Vein Endothelial Cells (HEC). Umbilical cords from uncomplicated deliveries of healthy women were collected within 2 d of birth in sterile glucose-containing PBS. HEC were isolated by standard techniques (Muller et al., J. Exp. Med., 1989; 170:399) from cannulated umbilical veins using collagenase at 75 U/ml. Harvested cells from each cord were plated as separate primary cultures in 25-cm$^2$ tissue culture flasks coated with human plasma fibronectin at >1 μg/cm$^2$. Cultures were washed free of nonadherent cells 4 h after initial plating and returned to culture in complete medium. Cultures isolated from cords >20 cm long generally reached confluence in 3-5 days.

Culture of HEC. Culture medium consisted of 20% normal human serum in medium 199. No exogenous growth factors were added. Medium was supplemented with penicillin and streptomycin (100 U/ml and 100 μg/ml, respectively). Medium was replaced every 3 d. Cultures were passaged at confluence by harvesting in trypsin/EDTA. Healthy primary isolates were pooled for passaging, and split generally at ratios of 1:2 to 1:4. Subcultures were grown on tissue culture plastic coated with human fibronectin (EC-fn) or on polymerized dehydrated collagen gels (EC-col) coated with fibronectin.

Collagen Gels. Vitrogen (Collagen Corp.) was mixed with 10× medium 199 and 0.1 N NaOH and pH adjusted to neutrality according to the manufacturer's directions. Tissue culture vessels were coated with appropriate volumes of the chilled, sterile solution (1.0 ml for a 35-mm dish, 8.0 ml for a 100-mm dish). The collagen was allowed to gel in the tissue culture incubator for up to 1 h; then sterile M199 was added to the dishes.

Silver Nitrate Staining. Silver nitrate staining of live or paraformaldehyde-fixed EC monolayers was performed as described (Muller et al., J. Exp. Med., 1989; 170:399).

Production of mAbs. HEC were grown to confluence on hydrated collagen gels. A test culture demonstrated strong $AgNO_3$ staining of intercellular junctions. HEC were non-enzymatically resuspended by rocking the culture flasks in 10 mM EDTA in HBSS. The recovered cells were washed and resuspended in Dulbocco's PBS (DPBS). Female $CD2F_1$ mice were immunized by injecting $6 \times 10^5$ live HEC in 0.25 ml DPBS via tail vein. The mice were subsequently boosted by an intravenous injection of $4 \times 10^5$ similarly prepared cells 1 and 4 mo later. 4d after the last boost, the spleen was removed from one mouse. A sterile suspension of spleen cells was fused with NS-1 myeloma cells at a 10:1 ratio using polyethylene glycol by standard methods (Muller et al., J. Exp. Med., 1989; 170:399). $3 \times 10^4$ cells were plated in each well of a 96-well tray and grown in HAT medium with 20% FCS.

Supernatants from growing hybridoma cultures were screened by immunoperoxidase simultaneously on confluent EC-col and EC-fn monolayers derived from the same patent culture and otherwise treated identically. Those supernatants that stained EC-col intensely in the region of intercellular junctions, but stained EC-fn with a diffuse surface pattern, were selected for cloning. The hydridomas were cloned on $CD2F_1$ thymocyte feeder layers and rescreened as above.

Clone hec2 was adapted to growth in 10% iron-supplemented calf serum (HyClone Laboratories, Logan, Utah) in RPMI medium.

The hybridoma Hec2.1, also described as clone hec2 for producing monoclonal antibody hec2, was deposited on Sep. 30, 2005, in the American Type Culture Collection (ATCC), 10801 University Boulevard, Manassas, Va. 20110-2209, under the provisions of the Budapest Treaty on the International Recognition of the Deposit of Microorganisms for the Purposes of Patent Procedure, and assigned ATCC Patent Deposit Designation No. PTA-7123.

Isotyping was performed on culture supernatants by ELISA using a mouse monoclonal sub-isotyping kit (HyClone Laboratories). The mAb reported here is an IgG1.

Example 3

HEC2 is CD99

TEM assays were repeated using purified hec2 IgG and obtained the same blockade. Hec2 is not generally toxic or inhibitory of leukocyte migration, since it has no effect on the reverse (basal→apical) transmigration of monocyte-derived dendritic cells in these cultures if administered to the cultured cells after TEM.

We first demonstrated that HEC2 is CD99 by the ability of hec2 to remove all of the immunoreactive antigen in an endothelial cell lysate that would be recognized by a commercially-available CD99 mAb (clone 013, Signet Labs, Dedham, Mass.), and vice-versa. Next, COS cells were transfected by a CD99 clone (Hahn et al., 1997, J. Immunol., 1:159(5):2250-8). Transfected cells, but not control cells, were recognized by hec2 as well as commercially available CD99 mAb by flow cytometry and immunofluorence.

Specifically, Cos cells were transiently transfected by electroporation with a cDNA clone of CD99 in pcDNA3 (Hahn et al., J. Immunol., 1997, 159:2550). On day three transfected cells or control Cos cells were nonenzymatically removed from the dishes with EDTA, washed, and incubated with commercial CD99 mAb (clone 013, Signet Labs, Dedham, Mass.) or hec2, washed and incubated with FITC-labeled goat-anti-mouse IgG before analysis by FACS®. Control Cos cells do not bind either the commercial CD99 mAb or hec2, respectively. Sixteen percent of the transected Cos cells stain positively with the commercial CD99, while approximately 25% of transected cells stain positively with hec2, bearing an even higher surface fluorescence. Transfected cells did not show any staining above background when probed with normal mouse serum and the secondary antibody. Transfected Cos cells on coverslips were also stained with hec2 followed by FITC-goat anti-mouse IgG and examined by immunofluorescence microscopy. Transfected cells show a bright plasma membrane staining pattern that stands out in contrast to nontransfected neighboring cells.

L cells have been transfected with this clone. Stable transfectants are selected for the experiments. A human leukocyte expression library is screened for the existence of other (alternatively spliced) cDNA clones. There is a report of one such form, but this has not been confirmed by other investigators. This clone is used to screen a murine thymocyte λ phage cDNA library for the murine equivalent of this molecule, which has not yet been described.

Example 4

Development of PECAM Deficient Transgenic Mice PECAM Knockout Mice

The murine PECAM clone (53) was used to make mice with a targeted deletion of the PECAM gene (26). Mice homozygous for the CD31 deletion are viable and born at the expected Mendelian frequency. They exhibit no obvious vascular defects and remain healthy and fertile with a normal lifespan. Circulating total leukocyte and platelet counts are similar to wild-type littermates. The PECAM knockout mice have approximately half the number of circulating PMN as wild-type littermates, but they are capable of responding to an inflammatory challenge with an intense neutrophilia.

In several models of acute inflammation, there was no significant difference between the knockouts and wild-type littermates in the numbers or types of leukocytes mobilized to the sites. The only observed defect in the inflammatory response noted to date is a subtle one: Neutrophils en route to a site of inflammation are temporarily trapped between the undersurface of the venular endothelium and the subendothelial basal lamina (26). This is reminiscent of the phenotype achieved with selective blocking of domain 6 of leukocyte PECAM (4,7); however, in the knockouts the delay is transient, as by 4 hours normal numbers of leukocytes have entered the site of inflammation (26). This implies that the delay in migration across basal lamina is compensated for at some other step in emigration.

Since these mice lack PECAM-1, but mobilize normal numbers of leukocytes to inflamed viscera at the same rate as wild-type mice, they must have expanded the use of PECAM-independent emigration pathways to make up for their lack of PECAM. These mice will be excellent models in which to study CD99/HEC2 TEM, since the role of CD99 in TEM can be studied in the absence of the strong influence of PECAM-1.

PECAM-Ig Expressing Mice

Three founder lines were generated using the transgene construct containing the ApoA1 promoter. Mice of all three lines were the same size and weight as their wild-type littermates. They were healthy and fertile and had normal ratios of male and female offspring. The mice were maintained in a clean [but not SPF] environment and were not susceptible to nosocomial infections [data not shown]. Quantitative PCR demonstrated that the transgene was expressed in the liver and lung, with lower levels in the kidney. The Tg11 strain showed expression in splenic tissue, which was not detected in the lower secreting Tg8 mice. The mice showed no spontaneous bleeding tendencies and their hematologic profiles were similar to their wild-type littermates.

The mice secreted intact murine PECAM-IgG into the circulation. Homozygous mice of the $Tg8_{20}$ line had plasma levels of about 20 µg/ml. Mice of the $Tg5_{1000}$ and $Tg11_{1000}$ lines generally expressed between 500 and 2,000 µg/ml. The higher levels of circulating PECAM-IgG in Tg11 correlated with increased message levels for the transgene, especially in the liver and lung, but not with intensity of hybridization signal on Southern blot. Immunoblot of transgenic serum demonstrated that the PECAM-IgG was running as a single band of 230 kD, the expected size of the intact dimerized form. These mice are described in greater detail in Liao, et al., 1999, J. Immunol., 163(10):5640-8.

Endogenous PECAM expression on the murine leukocytes was not changed by transgene expression. Similarly, the leukocytes expressed wild-type levels of CD11a, CD11b, and CD18. Even in mice expressing high levels of PECAM-IgG, the transgenic protein did not bind stably to the leukocytes, as previously found for human leukocytes and human PECAM-IgG in vitro, presumably reflecting the low numbers of PECAM molecules on these cells (6). This also demonstrates that the transgenic protein was not circulating bound via leukocyte Fe receptors. Control experiments demonstrated that human IgG could be readily detected if it were indeed bound by murine leukocyte FcRs. When heat aggregated human IgG was incubated with mouse blood, it bound to the leukocytes and remained bound through the preparation for FACS analysis. Due to the presence of PECAM-IgG in the plasma, tissues could not be accurately probed by immunoperoxidase to determine whether endogenous PECAM expression was altered on endothelial cells of the transgenic mice. However, quantitative PCR of lung, spleen, kidney, and liver showed no significant difference in endogenous PECAM message levels [per microgram of total RNA] among wild type, $Tg8_{20}$ or $Tg11_{1000}$ mice. No difference in staining pattern or intensity was detected between wild-type and any transgenic line when probed using antibodies against ICAM-1, ICAM-2, or VCAM-1. In the kidney specifically, ICAM-2 was expressed by endothelial cells of all vessels, including glomerular capillaries. ICAM-1 staining in kidneys was weak; VCAM-1 staining was focally and weakly present on endothelium of some of the larger microvessels, but was absent from peritubular and glomerular capillaries. Thus, except for the presence of circulating PECAM-IgG, the transgenic mice do not appear different from their wild-type littermates under basal conditions.

Leukocyte emigration is suppressed in $Tg8_{20}$ mice. Wild-type FVB/n mice and all strains of transgenic mice had similar numbers of mononuclear cells and virtually no PMN resident in their peritoneal cavities when unstimulated. When wild-type FVB/n mice were challenged with an intraperitoneal injection of thioglycollate broth and sacrificed 18 hours later, a dramatic inflammatory exudate including large numbers of neutrophils as well as monocytes was seen. In contrast, age-matched $Tg8_{20}$ littermates showed a marked blunting of the inflammatory response. Heterozygous Tg8 mice that have circulating mPECAM-IgG levels of 10 µg/ml showed a 50% reduction in PMN numbers; monocytes were reduced to near basal levels. In homozygous Tg820 mice producing 20 µg/ml, PMN infiltration was blocked by over 80%. This level of plasma mPECAM-IgG was similar to the levels that were achieved in experiments in which exogenously administered mPECAM-IgG was found to block PMN emigration into the peritoneal cavities of wild-type mice by 80% (6). Circulating leukocyte counts in $Tg8_{20}$ mice receiving thioglycollate broth were elevated at 18 hr, as had been seen previously with wild type mice receiving anti-PECAM reagents in the face of a thioglycollate challenge (2,6) consistent with the notion that leukocytes could be mobilized normally, but could not enter the site of inflammation.

The block in inflammation was at the level of transendothelial migration, as has been found previously (2,6). Histologic sections of tissues in the Tg8 mice showed PMN and Mo concentrated intravascularly in postcapillary venules, many apparently attached to the endothelial surface, but unable to transmigrate as occurs with anti-murine PECAM mAb (2) or exogenously administered mPECAM-IgG (6).

A surprising result came when evaluating the high producer lines of transgenic mice. $Tg5_{1000}$ and $Tg11_{1000}$ mice constitutively secreting supratherapeutic levels of mPECAM-IgG are paradoxically resistant to its effects. The response to intraperitoneal thioglycollate was virtually the same as for wild-type mice at both 3, 6 and 18 hours. Peritonitis in response to thioglycollate broth was blocked, as expected, in these strains by antibodies against CD11a and CD11b. This indicates that these mice were using leukocyte β2 integrins for adhering to the vascular wall and or transmigration.

$Tg5_{1000}$ and $Tg11_{1000}$ mice produce functional mPECAM-IgG. The failure of the transgenic protein to block leukocyte migration in the high producer mice was not due to defects in the transgenic protein itself: Serum or purified transgenic protein from these mice transferred to wild-type mice blocked inflammation well, and in a dose-dependent fashion.

Many chemoattractants, chemokines, and antibodies whose actions rely on cross-linking their ligands exhibit a bell-shaped dose-response curve. If the blocking effect of PECAM-IgG exhibited such properties, it was possible that the high levels of mPECAM-IgG in the plasma of $Tg5_{1000}$ and $Tg11_{1000}$ mice were well beyond the optimal inhibitory point and were, in fact, no longer effective. Alternatively, if PECAM-IgG bound to itself at high concentrations producing aggregates in which the binding sites of PECAM were already occupied, a decrease in efficacy as concentration rose above a certain threshold might be expected. To investigate this in a system that we could better manipulate, experiments were carried out in vitro using human leukocytes and endothelium, and human PECAM-IgG. In order to see whether there was a biphasic dose-response to PECAM-IgG in vitro, we carried out our transmigration assay exposing monocytes to concentrations of 1 mg/ml to 1 mg/ml PECAM-IgG. The results demonstrate that the plateau blockade by PECAM-IgG is maintained from 10 µg/ml [50 nM] up to the highest dose. Therefore, it is unlikely that the failure of $Tg5_{1000}$ and $Tg11_{1000}$ leukocytes to be blocked by the high concentrations of mPECAM-IgG circulating in their plasma is due to a decreased response to these concentrations.

$Tg5_{1000}$ and $Tg11_{1000}$ mice represent a unique system in which to study alternative transmigration pathways to PECAM. These mice do not use PECAM, even though their leukocytes and endothelial cells bear normal levels of it. Since none of their leukocytes are blocked by mPECAM-IgG, they may use different alternative pathways than those used by the 10-20% of wild-type leukocytes that are not blocked by exogenous mPECAM-IgG (6) or the 10-20% of leukocytes in the $Tg8_{20}$ mice that do transmigrate in the face of constant inhibitory levels of mPECAM-IgG, or the 100% of leukocytes of PECAM "knockout" mice that have never seen PECAM. CD99 may be crucial for a separate stage of TEM from PECAM. Alternatively, CD99 may play a role in the residual TEM that is PECAM-independent. In either case, it will be instructive to determine its role in these mice in which it can be studied independently of PECAM function.

Example 5

Transgenic Mouse Studies of CD99/HEC2

The role of HEC2 in TEM is tested in two separate models of acute inflammation in which we can distinguish a block in adhesion of leukocytes to endothelium from a block in TEM. The assays are the thioglycollate broth peritonitis assay and the croton oil ear swelling assay. In each assay, the effect of blocking the molecule is be quantitatively assessed for a role selectively on diapedesis. The role of these molecules in wild-type mice is examined to see what effect blocking them alone has on inflammation. Their role in $Tg8_{20}$ mice, in which PECAM function is maximally blocked is evaluated to see whether they complement the PECAM block, or require PECAM blockade to function. Their role in $Tg5_{1000}$ and $Tg11_{1000}$ mice is evaluated to see how they function under conditions where PECAM is not working, and in PECAM knockout mice to see how they function in the absence of PECAM. These latter two conditions may bring out roles for adhesion molecules that might not be obvious in wild-type mice where PECAM has a predominant role in TEM in these two animal models.

The Thioglycollate Broth-Induced Peritonitis Model

This model was successfully to assess the role of PECAM in TEM (2,6) and other adhesion molecules (72-74) in acute inflammation. Reagents [blocking mAb or CAM-IgG chimeras] are injected systemically and tested for their ability to block entry of leukocytes into the peritoneal cavity. The mesentery is harvested and examined microscopically to determine whether the block was at the level of adhesion or TEM. In several previous studies, this has strikingly demonstrated an arrest of leukocytes on the endothelium of mesenteric venules when TEM was blocked by mAb against PECAM (2) or mPECAM-IgG (6), but not when adhesion was blocked by mAb against CD11b. Test mAb or isotype control IgG are injected intravenously by tail vein. One hour later 1 ml of 4% thioglycollate broth is injected i.p. via 26G ⅜" needle. We normally examine the response to thioglycollate at 18 hours in order to see the effect of the experimental perturbations on both PMN and monocytes. Time courses are adjusted to shorter times [4-12 hours] in order to make the effect on PMN more pronounced and later times [up to 4 days] when the effect on Mo is more pronounced. At the time of assay, the mice are sacrificed. Peritoneal cells are isolated by lavage in Hanks' Balanced Salt Solution. Total peritoneal cell numbers are quantitated and differential counts are performed on Wright-Giemsa-stained cytospins. Peripheral blood is collected for total WBC count and differential smear. It is important to be certain that a decrease in leukocytes entering the peritoneal cavity is not due to reduced numbers in the circulation. Selected organs are also harvested at this time, including the mesentery, which is fixed in formalin for histologic examination.

The Croton Oil Dermatitis Assay

This is an assay of nonspecific inflammation in which 10 ml of croton oil [2% in a 4:1 mixture of acetone:olive oil] is applied to one ear of a mouse (72). The contralateral ear receives 10 ml of carrier and serves as an internal control for background inflammation. Croton oil produces an acute inflammatory response in which the affected ear becomes red and swollen. Histologically, there is mast cell degranulation and recruitment of leukocytes out of the local venules into the soft tissues in the dermis of the ear. In our hands maximum leukocyte emigration [predominantly PMN] occurs 8 hours after application of the irritant. Reagents to be tested for their ability to block TEM are injected intraperitoneally one hour before application of croton oil.

Mice are sacrificed, both ears removed, and several cross-sections are examined to quantitate leukocyte efflux. This can be done manually or using image analysis software to quantitate $PMN/mm^2$. Alternatively, anti-PMN mAb with a fluorescent tag can be applied, and total fluorescence quantitated using a phosphorimager. Careful histologic examination of the ears will also tell us whether the block is at the level of TEM or adhesion. Blocking TEM results in accumulation of PMN on the venular walls [FIG. 12]. This is also a good system in which to test the possibility that PECAM knockout or PECAM resistant mice [high dose transgenics] emigrate via a different vascular route [e.g. capillaries rather than venules], since the leukocytes tend to stay relatively close to the vessels they emigrated from in this model.

The Role of HEC2 in TEM mAb against the murine form of HEC2 is tested for their ability to block in these models. mAb is expected to inhibit TEM in vivo the way hec2 inhibits TEM of human cells in vivo. Purified, sterile, endotoxin-free Fab amd F[ab']2 fragments of mAb against murine HEC2 are tested.

Wild-type mice. Since hec2 blocks TEM in the absence of PECAM blockade, the murine form is expected to would work similarly in vivo. Leukocyte emigration is markedly inhibited by optimal concentrations of mAb against murine HEC2. The ears and mesenteric venules of mice are examined. A selective block in TEM should result in an increase in leukocytes on the vessel wall that reflects the decreased emigration of these cells. However, if HEC2 is involved in an earlier stage of TEM than PECAM, it is possible that blocking HEC2 in vivo will not produce the phenotype of leukocytes arrested on the vessel wall. If interruption of interaction with HEC2 does not leave them firmly adherent to the endothelium by some other mechanism, they may be carried off in the flow of the bloodstream, and the phenotype produced in vitro under static conditions would not be seen, despite a dramatic reduction in leukocytes that emigrate.

Tg820 mice. The combined action of hec2 and anti-PECAM antibody in vitro was so complete that it bears testing in vivo. The near total block of TEM is evident in this case, and it is be clinically important to know whether blocking any two molecules on leukocytes or endothelium could produce such a complete block in vivo. Blocking murine HEC2 and murine PECAM is expected to produce a near-total block in leukocyte emigration. This is tested by injecting mAb against murine HEC2 into the $Tg8_{20}$ mice, in whom PECAM is maximally blocked. We predict that it may be difficult, if not impossible, to discern the site of the blockade in vivo, since the $Tg8_{20}$ mice already show so many of their leukocytes arrested on the vessel wall. However, the quantitative decrease in leukocytes in the peritoneal cavity or the dermis of the ear should be noticeable.

$Tg5_{1000}$ and $Tg11_{1000}$ mice. In these mice PECAM-independent pathways of TEM predominate, since these mice do not seem to use their own PECAM. Monoclonal Ab against murine HEC2 may have an even larger effect than in the wild-type mice. The same caveat about potentially blocking adhesion more than transmigration under flow conditions holds here as it did for wild-type mice.

PECAM-deficient [knockout] mice. PECAM knockout mice must use PECAM-independent pathways for TEM. They mobilize the same numbers and types of leukocytes to sites of inflammation as wild-type mice, so they have expanded their use of these pathways to support normal levels of TEM. Under these conditions, it is simple to see an effect of blocking an alternate adhesion molecule. It is be instructive to determine whether the molecules knockout mice use for TEM are the same as those used by mice that have PECAM, but cannot use it [e.g., $Tg5_{1000}$ and $Tg11_{1000}$].

Example 6

T Cell Transendothelial Migration is Mediated by CD99/HEC2

HUVEC monolayers on collagen gels were preincubated for three hours in the presence or absence of stromal derived factor-1 (SDF-1), then washed before addition of partially-purified T cells. Peripheral blood mononuclear cells were freshly obtained from human volunteers via Ficoll-Hypaque gradient centrifugation by standard methods. The T cells were derived from these cells by allowing monocytes and some B lymphocytes to adhere to plastic tissue culture dishes for thirty minutes. Non-adherent cells were collected and resuspended to $2\times10^6$ cells/ml in M199 culture medium containing 2% Human Serum, optionally in the presence of the indicated monoclonal antibodies at 20 micrograms/ml. The cell suspension was added tot he tops of the HUVEC monolayers and transendothelial migration was allowed to proceed for four hours at 37° C. The co-cultures were then washed and fixed in glutaraldehyde, stained, and examined by Nomarsky optics (exactly as for monocyte and neutrophil TEM). The percentage of cells transmigrating (% TEM) was calculated by dividing the number of cells below the HUVEC monolayer by the total number (adherent plus transmigrated) of cells in that field. At least three fields in three or more monolayers for each condition were examined. The bars show the mean +/- the standard derivation for these measurements. hec7=mAb against PECAM-1 (CD31); IB4=mAb against the leukocyte integrin beta chain (CD18); 84H10=mAb against intercellular adhesion molecule-1 (ICAM-1).

Unfractionated peripheral blood mononuclear cells from which the T cells were derived were also tested as a positive control. This population contains most of the monocytes, so the % TEM is much higher than with isolated T cells.

Example 7

CD99 is Used for Transendothelial Migration of Monocytes

The standard assay for transendothelial migration uses human blood mononuclear cells added to human endothelial cell monolayers grown to confluence on hydrated collagen gels. We have found that CD99 is expressed both on monocytes and concentrated at endothelial cell junctions. Our anti-CD99 monoclonal antibody blocks the transmigration of monocytes by greater than 90% in our assay. Monocytes blocked by anti-CD99 become polarized and extend through the endothelial junctions, but are unable to completely cross the endothelial monolayer CD99 appears to interact homophilically between monocytes and the endothelial cells. CD99 transfected mouse L cells also cluster in a homophilic fashion in adhesion assays. In particular, we have expressed the human clone in L cell fibroblasts Expression of CD99 in these cells imparts on them the ability to adhere to each other in a homophilic manner. That is, CD99 on one cell binds to CD99 on the apposing cell. These studies were carried out in suspension, in a similar manner to studies published several years ago using PECAM and VE-cadherin transfected cells. The anti-CD99 monoclonal antibody (mAb), hec2, blocked the ability of the CD99 transfectants to adhere to each other, consistent with its role in blocking CD99-mediated transendothelial migration of leukocytes.

Experimental data show that CD99 is involved with a step in transendothelial migration that is distal to (later in time or "downstream" of) the step controlled by PECAM. When transmigration is blocked by anti-PECAM reagents, then that block is removed, anti-CD99 can still block transmigration. On the other hand, when transmigration is blocked at the CD99 step by hec2, then that block removed, anti-PECAM reagents are no longer able to block. Consistent with this, monocytes arrested in transmigration appear to have part of their cytoplasm beneath the endothelial cell, while the trailing uropod remains on the apical surface.

REFERENCES

1. Muller, W. A., S. A. Weigl, X. Deng, and D. M. Phillips. 1993. PECAM-1 is required for transendothelial migration of leukocytes. J. Exp. Med. 178:449-460.
2. Bogen, S., J. Pak, M. Garifallou, X. Deng, and W. A. Muller. 1994. Monoclonal antibody to murine PECAM-1 [CD31] blocks acute inflammation in vivo. J. Exp. Med. 179:1059-1064.
3. Berman, M. E. and W. A. Muller. 1995. Ligation of platelet/endothelial cell adhesion molecule 1 (PECAM-1/CD31) on monocytes and neutrophils increases binding capacity of leukocyte CR3 (CD11b/CD18). J. Immunol. 154:299-307.
4. Liao. F., H. K. Huynh, A. Eiroa, T. Greene, E. Polizzi, and W. A. Muller. 1995. Migration of monocytes across endothelium and passage through extracellular matrix involve separate molecular domains of PECAM-1. J. Exp. Med. 182:1337-1343.
5. Berman, M. E., Y. Xie, and W. A. Muller. 1996. Roles of platelet/endothelial cell adhesion molecule-1 (PECAM-1, CD31) in natural killer cell transendothelial migration and beta 2 integrin activation. J. Immunol. 156:1515-1524.
6. Liao, F., J. Ali, T. Greene, and W. A. Muller. 1997. Soluble domain 1 of platelet-endothelial cell adhesion molecule (PECAM) is sufficient to block transendothelial migration in vitro and in vivo. J. Exp. Med. 185:1349-1357.
7. Muller, W. A., T. Greene, and F. Liao. 1997. Transendothelial migration and interstitial migration of monocytes are mediated by separate domains of monocyte CD31. In Leukocyte Typing VI. Proceedings of the VIth International Leukocyte Differentiation Antigen Workshop, Kobe, Japan, 1996. T. Kishimoto, editor. Garland Publishers, London. 370-372.
8. Vaporciyan, A. A., H. M. Delisser, H.-C. Yan, I. I. Mendiguren, S. R. Thom, M. L. Jones, P. A. Ward, and S. M. Albelda. 1993. Involvement of platelet-endothelial cell adhesion molecule-1 in neutrophil recruitment in vivo. Science 262:1580-1582.
9. Wakelin, M. W., M.-J. Sanz, A. Dewar, S. M. Albelda, S. W. Larkin, N. Boughton-Smith, T. J. Williams, and S. Nourshargh. 1996. An anti-platelet/endothelial cell adhesion molecule-1 antibody inhibits leukocyte extravasation from mesenteric microvessels in vivo by blocking the passage through basement membrane. J. Exp. Med. 184: 229-239.
10. Murohara, T., J. A. Delyani, S. M. Albelda, and A. M. Lefer. 1996. Blockade of platelet endothelial cell adhesion molecule-1 protects against myocardial ischemia and reperfusion injury in cats. J. Immunol. 156:3550-3557.
11. Christofidou-Solomidou. M., M. T. Nakada, J. Williams, W. A. Muller, and H. M. Delisser. 1997. Neutrophil platelet endothelial cell adhesion molecule-1 participates in neutrophil recruitment at inflammatory sites and is down-regulated after leukocyte extravasation. J. Immunol. 158:4872-4878.
12. Gumina, R. J., J. E. Schultz, Z. Yao, D. Kenny, D. C. Warltier, P. J. Newman, and G. J. Gross. 1996. Antibody to platelet/endothelial cell adhesion molecule-1 reduces myocardial infarct size in a rat model of ischemia-reperfusion injury. Circulation 94:3327-3333.
13. Ross, R. 1993. The pathogenesis of atherosclerosis: a perspective for the 1990s. Nature 362:801-809.
14. Lasky, L. A. 1992. Selectins: Interpreters of cell-specific carbohydrate information during inflammation. Science 258:964-969.
15. Springer, T. A. 1994. Traffic signals for lymphocyte recirculation and leukocyte emigration: The multistep paradigm. Cell 76:301-314.
16. Lo, S. K., S. Lee, R. A. Ramos, R. Lobb, M. Rosa, G. Chi-Rosso, and S. D. Wright. 1991. Endothelial-leukocyte adhesion molecule 1 stimulates the adhesive activity of leukocyte integrin CD3 [CD11B/CD18, Mac-1, alpha m beta 2] on human neutrophils. J. Exp. Med. 173:1493-1500.
17. Lorant, D. E., K. D. Patel, T. M. McIntyre, R. P. McEver, S. M. Prescott, and G. A. Zimmerman. 1991. Coexpression of GMP-140 and PAF by endothelium stimulated by histamine or thrombin: A juxtacrine system for adhesion and activation of neutrophils. J. Cell Biol. 115:223-234.
18. Hermanowski-Vosatka, A., J. A. G. Van Strijp, W. J. Swiggard, and S. D. Wright. 1992. Integrin modulating factor-1: A lipid that alters the function of leukocyte integrins. Cell 68:341-352.
19. Tanaka, Y., D. H. Adams, S. Hubscher. H. Hirano, U. Siebenlist, and S. Shaw. 1993. T-cell adhesion induced by proteoglycan-immunobilized cytokine MIP-1 beta. Nature 361:79-82.
20. Huber, A. R., S. L. Kunkel, R. F. Todd, III, and S. J. Weiss. 1991. Regulation of transendothelial neutrophil migration by endogenous interleukin-8. Science 254:99-102.
21. Tanaka, Y., S. M. Albelda, K. J. Horgan, G. A. Van Seventer, Y. Shimizu, W. Newman, J. Hallam, P. J. Newman, C. A. Buck, and S. Shaw. 1992. CD31 expressed on distinctive T cell subsets is a preferential amplifier of beta1 integrin-mediated adhesion. J. Exp. Med. 176:245-253.
22. Piali, L., S. M. Albelda, H. S. Baldwin, P. Hammel, R. H. Gisler, and B. A. Imhof. 1993. Murine platelet endothelial cell adhesion molecule (PECAM-1/CD31) modulates beta2 integrins on lymphokine-activated killer cells. Eur. J. Immunol. 23:2464-2471.
23. Meerschaert, J. and M. B. Furie. 1994. Monocytes use either CD11/CD18 or VLA-4 to migrate across human endothelium in vitro. J. Immunol. 152:1915-1926.
24. Newman, P. J., M. C. Berndt, J. Gorski, G. C. White II, S. Lyman, C. Paddock, and W. A. Muller. 1990. PECAM-1 [CD31] cloning and relation to adhesion molecules of the immunoglobulin gene superfamily. Science 247:1219-1222.
25. Sun, Q.-H., H. M. Delisser, M. M. Zukowski, C. Paddock, S. M. Albelda, and P. J. Newman. 1996. Individually distinct Ig homology domains in PECAM-1 regulate homophilic binding and modulate receptor affinity. J. Biol. Chem. 271:11090-11098.
26. Duncan, G. S., D. P. Andrew, H. Takimoto, S. A. Kaufman, H. Yoshida, J. Spellberg, J. L. de la Pompa, A. Elia, A. Wakeham, B. Karan-Tamir, W. A. Muller, G. Sendali, M. M. Zukowski, and T. W. Mak. 1999. Genetic evidence for functional redundancy of platelet/endothelial cell adhesion molecule-1 (PECAM-1): CD31-deficient mice reveal PECAM-1-dependent and PECAM-1-independent functions. J. Immunol. 162:3022-3030.
27. Tang, Q. and R. L. Hendricks, 1996. Interferon gamma regulates platelet endothelial cell adhesion molecule-1 expression and neutrophil infiltration into herpes simplex virus-infected mouse corneas. J Exp Med 184:1435-1447.
28. Feng, D., J. A. Nagy, K. Pyne, H. F. Dvorak, and A. M. Dvorak. 1998. Neutrophils emigrate from venules by a transendothelial cell pathway in response to fMLP. J. Exp. Med. 187:903-915.
29. Ali, J., F. Liao, E. Martens, and W. A. Muller. 1997. Vascular endothelial cadherin (VE-Cadherin): Cloning and role in endothelial cell-cell adhesion. Microcirculation 4:267-277.
30. Lampugnani, M. G., M. Resnati, M. Raiteri, R. Pigott, A. Piscane, G. Houen, L. P. Ruco, and E. Dejana. 1992. A novel endothelial-specific membrane protein is a marker of cell-cell contacts. J. Cell. Biol. 118:1511-1522.
31. Gotsch, U., E. Borges, R. Bosse, E. Boggemeyer, M. Simon, H. Mossmann, and D. Vestweber. 1997. VE-cadherin antibody accelerates neutrophil recruitment in vivo. J. Cell Sci. 110:583-588.
32. de Fougerolles, A. R., S. A. Stacker, R. Schwarting, and T. A. Springer. 1991. Characterization of ICAM-2 and evidence for a third counter-receptor for LFA-1. J. Exp. Med. 174:253-267.
33. Xu, H., I. L. Tong, A. R. de Fougerolles, and T. A. Springer, 1992. Isolation, characterization, and expression of mouse ICAM-2 complementary and genomic DNA. J. Immunol. 149:2650-2655.
34. Xie, J., R. Li, P. Kotovuri, C. Vermot-Desroches, J. Wijdenes, M. Arnaout, P. Nortamo, and C. G. Gahmberg. 1995. Intercellular adhesion molecule-2 (CD102) binds to the leukocyte integrin CD11b/CD18 through the A domain. J. Immunol. 155:3619-3628.
35. Martin-Padura. I., S. Lostaglio, M. Schneemann, L. Williams, M. Romano, P. Fruscella, C. Panzeri, A. Stoppacciaro, L. Ruco, A. Villa, D. Simmons, and E. Dejana. 1998. Junctional adhesion molecule, a novel member of the immunoglobulin superfamily that distributes at intercellular junctions and modulates monocyte transmigration. J. Cell Biol. 142:117-127.

36. Naik, U. P., Y. H. Ehrlich, and E. Kornecki. 1995. Mechanisms of platelet activation by a stimulatory antibody: Cross-linking of a novel platelet receptor for monoclonal antibody F11 with the FcgammaRII receptor. Biochem. J. 310:155-162.

37. Furuse, M., T. Hirase, M. Itoh, A. Nagafuchi, S. Yonemura, S. Tsukita, and S. Tsukita. 1993. Occludin: A novel integral membrane protein localizing at tight junctions. J. Cell Biol. 123:1777-1788.

38. McCarthy, K. M., I. B. Skare, M. C. Stankewich, M. Furuse, S. Tsukita, R. A. Rogers, R. D. Lynch, and E. E. Schneeberger. 1996. Occludin is a functional component of the tight junction. J. Cell Sci. 109:2287-2298.

39. Fujimoto, K. 1995. Freeze-fracture replica electron microscopy combined with SDS digestion for cytochemical labeling of integral membrane proteins. Application to the immunogold labeling of intercellular junctional complexes. J. Cell Sci. 108:3443-3449.

40. Saitou, M., K. Fujimoto, Y. Doi, M. Itoh, T. Fujimoto, M. Furuse, H. Takano, T. Noda, and S. Tsukita. 1998. Occludin-deficient embryonic stem cells can differentiate into polarized epithelial cells bearing tight junctions. J. Cell Biol. 141:397-408.

41. Furuse, M., K. Fujita, T. Hiiragi, K. Fujimoto, and S. Tsukita. 1998. Claudin-1 and -2: Novel integral membrane proteins localizing at tight junctions with no sequence similarity to occludin. J. Cell Biol. 141:1539-1550.

42. Morita, K. H. Sasaki, K. Fujimoto. M. Furuse, and S. Tsukita. 1999. Claudin-11/OSP-based tight junctions of myelin sheaths in brain and sertoli cells in testis. J. Cell Biol. 145:579-588.

43. Morita, K., M. Furuse, K. Fujimoto, and S. Tsukita. 1999. Claudin multigene family encoding four-transmembrane domain protein components of tight junction strands. Proc. Natl. Acad. Sci. USA 96:511-516.

44. Muller, W. A. 1996. Transendothelial migration of leukocytes. In Leukocyte recruitment in inflammatory disease. G. Peltz, editor. R. G. Landis Company. Austin, Tex. 3-18.

45. Muller, W. A. and S. Weigl. 1992. Monocyte-selective transendothelial migration: Dissection of the binding and transmigration phases by an in vitro assay. J. Exp. Med. 176:819-828.

46. Butcher, E. C. 1991. Leukocyte-endothelial cell recognition: three (or more) steps to specificity and diversity. Cell 67:1033-1036.

47. Carlos, T. M. and J. M. Harlan. 1994. Leukocyte-Endothelial Cell Adhesion Molecules. Blood 84:2068-2101.

48. Muller, W. A., C. M. Ratti, S. L. McDonnell, and Z. A. Cohn. 1989. A human endothelial cell-restricted, externally disposed plasmalemmal protein enriched in intercellular junctions. J. Exp. Med. 170:399-414.

49. Albelda, S. M., W. A. Muller, C. A. Buck, and P. J. Newman. 1991. Molecular and cellular properties of PECAM-1 [endoCAM/CD31]: A novel vascular cell-cell adhesion molecule. J. Cell Biol. 114:1059-1068.

50. Muller, W. A. 1992. PECAM-1: an adhesion molecule at the junctions of endothelial cells. In Mononuclear Phagocytes. The Proceedings of the Fifth Leiden Meeting on Mononuclear Phagocytes. R. van Furth, Z. A. Cohn, and S. Gordon, editors. Blackwell Publishers, London. 138-148.

51. Shang, X. Z. and A. C. Issekutz. 1998. Contribution of CD11a/CD18, CD11b/CD18, ICAM-1 (CD54) and -2 (CD102) to human monocyte migration through endothelium and connective tissue fibroblast barriers. Eur. J. Immunol. 28:1970-1979.

52. Issekutz, A. C., D. Rowter, and T. A. Springer. 1999. Role of ICAM-1 and ICAM-2 and alternate CD11/CD18 ligands in neutrophil transendothelial migration. J. Leuk. Biol. 65:117-126.

53. Xie, Y. and W. A. Muller. 1993. Molecular cloning and adhesive properties of murine platelet/endothelial cell adhesion molecule-1. Proc. Natl. Acad. Sci. USA 90:5569-5573.

54. Kostrikis, L. G., Y. Huang, J. P. Moore, S. M. Wolinsky, L. Zhang, Y. Guo, L. Deutsch, J. Phair, A. U. Neumann, and D. D. Ho. 1998. A chemokine receptor CCR2 allele delays HIV-1 disease progression and is associated with a CCR5 promoter mutation. Nat. Med. 4:350-353.

55. McElrath, M. J., G. Kaplan, A. Nusrat, and Z. A. Cohn. 1987. Cutaneous leishmaniasis. The defect in T cell influx in BALB/c mice. J. Exp. Med. 165:546-559.

56. Smith, C. W., T. K. Kishimoto, O. Abbass, B. Hughes, R. Rothlein, L. V. McIntire, E. Butcher, and D. C. Anderson. 1991. Chemotactic factors regulate lectin adhesion molecule 1 (LECAM-1)-dependent neutrophil adhesion to cytokine-stimulated endothelial cells in vitro. J. Clin. Invest. 87:609-618.

57. Muller, W. A., R. M. Steinman, and Z. A. Cohn. 1980. The membrane proteins of the vacuolar system. I. Analysis by a novel method of intralysosomal iodination. J. Cell Biol. 86:292-303.

58. Muller, W. A., R. M. Steinman, and Z. A. Cohn. 1980. The membrane proteins of the vacuolar system. II. Bidirectional flow between secondary lysosomes and plasma membrane. J. Cell Biol. 86:304-314.

59. Muller, W. A. and M. A. Gimbrone Jr. 1986. Plasmalemmal proteins of cultured vascular endothelial cells exhibit apical-basal polarity: Analysis by surface-selective iodination. J. Cell Biol. 103:2389-2402.

60. Pober, J. S., M. P. Bevilacqua, D. L. Mendrick, L. A. Lapierre, W. Fiers, and M. A. Gimbrone. 1986. Two distinct monokines, interleukin 1 and tumor necrosis factor, each independently induce biosynthesis and transient expression of the same antigen on the surface of cultured human vascular endothelial cells. J. Immunol. 136:1680-1687.

61. Romer, L. H., N. V. McLean, Y. Horng-Chin, M. Daise, J. Sun, and H. M. Delisser. 1995. IFN-gamma and TNF-alpha induce redistribution of PECAM-1 [CD31] on human endothelial cells. J. Immunol 154:6582-6592.

62. Aruffo, A. and B. Seed. 1987. Molecular cloning of CD28 cDNA by a high-efficiency COS cell expression system. Proc. Natl. Acad. Sci. USA 84:8573-8577.

63. Seed, B. and A. Aruffo. 1987. Molecular cloning of the CD2 antigen, the T-cell erythrocyte receptor, by a rapid immunoselection procedure. Proc. Natl. Acad. Sci. USA 84:3365-3369.

64. Maniatis, T., E. F. Fritsch, and J. Sambrook. 1982. Molecular Cloning: A Laboratory Manual. Anonymous Cold Spring Harbor Laboratories, Cold Spring Harbor, N.Y. 191-192.

65. Muller, W. A., M. E. Berman, P. J. Newman, H. M. Delisser, and S. M. Albelda. 1992. A heterophilic adhesion mechanism for Platelet/Endothelial Cell Adhesion Molecule-1 [CD31]. J. Exp. Med. 175:1401-1404.
66. Huang, A. J., J. E. Manning, T. M. Bandak, M. C. Ratau, K. R. Hanser, and S.C. Silverstein. 1993. Endothelial cell cytosolic free calcium regulates neutrophil migration across monolayers of endothelial cells. J. Cell Biol. 120: 1371-1380.
67. DiVirgilio. F., T. H. Steinberg, J. A. Swanson, and S.C. Silverstein. 1988. Fura-2 secretion and sequestration in macrophages. J. Immunol. 140:915-920.
68. Galfre, G., S.C. Howe, C. Milstein, G. N. Butcher, and J. C. Howard. 1977. Antibodies to major histocompatibility antigens produced by hybrid cell lines. Nature 266: 550-552.
69. Mishell, B. B. and S. M. Shiigi. 1980. Selected methods in cellular immunology. W. H. Freeman, San Francisco.
70. Reilly, P. L., J. R. J. Woska, D. D. Jeanfavre, E. McNally, R. Rothlein, and B. J. Bormann. 1995. The native structure of intercellular adhesion molecule-1 (ICAM-1) is a dimer. Correlation with binding to LFA-1. J. Immunol. 155:529-532.
71. Miller, J., R. Knorr, M. Ferrone, R. Houdei, C. P. Carron, and M. L. Dustin. 1995. Intercellular adhesion molecule-1 dimerization and its consequences for adhesion mediated by lymphocyte function associated molecule-1. J Exp Med 182:1231-1241.
72. Mizgerd, J. P., H. Kubo, G. J. Kutkoski, S. D. Bhagwan, K. Scharffeter-Kochanek, A. L. Beaudet, and C. M. Doerschuk. 1997. Neutrophil emigration in the skin, lungs, and peritoneum: Different requirements for CD11/CD18 revealed by CD18-deficient mice. J. Exp. Med. 186:1357-1364.
73. Mayadas, T. N., R. C. Johnson, H. Rayburn, R. O. Hynes, and D. D. Wagner. 1993. Leukocyte rolling and extravasation are severely compromised in P selectin-deficient mice. Cell 74:541-554.
74. Watson, S. R., C. Fennie, and L. A. Lasky. 1991. Neutrophil influx into an inflammatory site inhibited by a soluble homing receptor-IgG chimaera. Nature (London) 349:164-167.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all values are approximate, and are provided for description.

All patents, applications, publications, test methods, literature, and other materials cited herein are hereby incorporated by reference.

What is claimed is:

1. A method of inhibiting transendothelial migration (TEM) of leukocytes in a subject, comprising administering to the subject a CD99 binding inhibitor, wherein the CD99 binding inhibitor is an anti-CD99 antibody molecule, and wherein CD99-mediated leukocyte transmigration through the endothelium is inhibited.

2. The method according to claim 1, wherein the CD99 is located on endothelial cells.

3. The method according to claim 1, wherein the CD99 is located on the leukocytes.

4. The method according to claim 1 wherein the TEM occurs between activated endothelial cells.

5. The method according to claim 4, wherein the activated endothelial cells are activated as a result of contact with a pro-inflammatory cytokine selected from the group consisting of tumor necrosis factor (TNF) and interleukin-1 (IL-1).

6. The method according to claim 1, wherein the TEM occurs across endothelial cells in a tissue selected from the group consisting of arterial endothelium, venous endothelium, venular endothelium, and post-capillary venular endothelium.

7. The method according to claim 1, wherein TEM occurs into a site of inflammation.

8. The method according to claim 1, wherein inhibiting CD99-mediated transmigration of leukocytes comprises contacting the leukocytes, the endothelium, or both with an anti-CD99 antibody molecule.

9. The method according to claim 1, wherein the anti-CD99 antibody molecule is monoclonal antibody hec2 (ATCC deposit PTA-7123).

10. A method according to claim 9, wherein the anti-CD99 antibody molecule is a humanized or chimeric antibody.

11. The method according to claim 1, wherein the anti-CD99 antibody molecule is a polyclonal antibody.

12. The method according to claim 1, wherein the anti-CD99 antibody molecule is a monoclonal antibody.

13. The method according to claim 1, wherein the anti-CD-99 antibody molecule is selected from the group consisting of a humanized, chimeric, and human antibody.

* * * * *